(12) United States Patent
May

(10) Patent No.: US 9,937,166 B2
(45) Date of Patent: Apr. 10, 2018

(54) USE OF LEVOCETIRIZINE AND MONTELUKAST IN THE TREATMENT OF TRAUMATIC INJURY

(71) Applicant: INFLAMMATORY RESPONSE RESEARCH, INC., Santa Barbara, CA (US)

(72) Inventor: Bruce Chandler May, Santa Barbara, CA (US)

(73) Assignee: Inflammatory Response Research, Inc., Santa Barbara, CA (US)

( * ) Notice: Subject to any disclaimer, the term of this patent is extended or adjusted under 35 U.S.C. 154(b) by 0 days.

(21) Appl. No.: 15/348,253

(22) Filed: Nov. 10, 2016

(65) Prior Publication Data

US 2017/0056395 A1 Mar. 2, 2017

Related U.S. Application Data

(63) Continuation of application No. 14/831,469, filed on Aug. 20, 2015, now Pat. No. 9,522,148, which is a continuation of application No. PCT/US2014/021706, filed on Mar. 7, 2014.

(60) Provisional application No. 61/780,336, filed on Mar. 13, 2013.

(51) Int. Cl.
| | |
|---|---|
| *A61K 31/495* | (2006.01) |
| *A61K 38/14* | (2006.01) |
| *A61K 45/06* | (2006.01) |
| *A61K 31/407* | (2006.01) |
| *A61K 31/424* | (2006.01) |
| *A61K 31/43* | (2006.01) |
| *A61K 31/431* | (2006.01) |
| *A61K 31/47* | (2006.01) |
| *A61K 31/496* | (2006.01) |
| *A61K 31/505* | (2006.01) |
| *A61K 31/5383* | (2006.01) |
| *A61K 31/546* | (2006.01) |
| *A61K 31/635* | (2006.01) |
| *A61K 31/65* | (2006.01) |
| *A61K 31/7052* | (2006.01) |
| *A61K 31/7056* | (2006.01) |

(52) U.S. Cl.
CPC .......... *A61K 31/495* (2013.01); *A61K 31/407* (2013.01); *A61K 31/424* (2013.01); *A61K 31/43* (2013.01); *A61K 31/431* (2013.01); *A61K 31/47* (2013.01); *A61K 31/496* (2013.01); *A61K 31/505* (2013.01); *A61K 31/5383* (2013.01); *A61K 31/546* (2013.01); *A61K 31/635* (2013.01); *A61K 31/65* (2013.01); *A61K 31/7052* (2013.01); *A61K 31/7056* (2013.01); *A61K 38/14* (2013.01); *A61K 45/06* (2013.01)

(58) Field of Classification Search
CPC ....... A61K 31/495; A61K 31/47; A61K 31/56
USPC ............................................. 514/171, 255.04
See application file for complete search history.

(56) References Cited

U.S. PATENT DOCUMENTS

| | | | |
|---|---|---|---|
| 4,801,612 A | | 1/1989 | Wei et al. |
| 5,147,637 A | * | 9/1992 | Wright ............... C07K 16/2845 424/143.1 |
| 5,540,225 A | * | 7/1996 | Schutt .................. A61K 9/0026 128/207.15 |
| 6,384,038 B1 | | 5/2002 | Rubin |
| 6,790,849 B2 | | 9/2004 | Rubin |
| 7,166,640 B2 | | 1/2007 | Berg |
| 7,291,331 B1 | | 11/2007 | Croft et al. |
| 9,044,479 B2 | | 6/2015 | May |
| 9,522,148 B2 | | 12/2016 | May |
| 2002/0052312 A1 | | 5/2002 | Reiss et al. |
| 2006/0263350 A1 | | 11/2006 | Lane |
| 2007/0020352 A1 | | 1/2007 | Tripp et al. |
| 2007/0025987 A1 | | 2/2007 | Brunetta |
| 2007/0244128 A1 | | 10/2007 | Hutchinson et al. |
| 2008/0260644 A1 | | 10/2008 | Cohen |
| 2010/0305080 A1 | * | 12/2010 | O'Shea ................. C07D 215/18 514/171 |
| 2012/0040892 A9 | | 2/2012 | Zimmer et al. |
| 2012/0053563 A1 | | 3/2012 | Du |
| 2012/0071509 A1 | | 3/2012 | Gore et al. |
| 2012/0190691 A1 | * | 7/2012 | Bouyssou .......... A61K 31/4402 514/255.04 |
| 2013/0011395 A1 | | 1/2013 | Spies et al. |

(Continued)

FOREIGN PATENT DOCUMENTS

| | | |
|---|---|---|
| EP | 2 520 292 | 7/2012 |
| JP | 2001-526232 | 12/2001 |

(Continued)

OTHER PUBLICATIONS

Bisgaard Hans, "A Randomized Trial of Montelukast in Respiratory Syncytial Virus Postbronchiolitis", American Journal of Respiratory and Critical Care Medicine, 2003, vol. 167, No. 3, pp. 379-383.

(Continued)

*Primary Examiner* — Jennifer M Kim
(74) *Attorney, Agent, or Firm* — Knobbe, Martens, Olson & Bear, LLP

(57) ABSTRACT

The embodiments described herein include methods and formulations for treating lung and brain injury. The methods and formulations include, but are not limited to, methods and formulations for delivering effective concentrations of levocetirizine and montelukast to a patient in need. The methods and formulations can comprise conventional and/or modified-release elements, providing for drug delivery to the patient.

11 Claims, 9 Drawing Sheets

(56) References Cited

U.S. PATENT DOCUMENTS

| | | |
|---|---|---|
| 2013/0029949 A1 | 1/2013 | Hoffmann et al. |
| 2013/0030000 A1 | 1/2013 | Chobanian et al. |
| 2015/0231133 A1 | 8/2015 | May |
| 2016/0175301 A1 | 6/2016 | May |

FOREIGN PATENT DOCUMENTS

| | | |
|---|---|---|
| JP | 2002-511425 | 4/2002 |
| JP | 2011-500847 | 1/2011 |
| KR | 10-2001-0033485 | 4/2001 |
| WO | WO 95/009652 | 4/1995 |
| WO | WO 99/032125 | 7/1999 |
| WO | WO 99/052553 | 10/1999 |
| WO | WO 03/002098 | 1/2003 |
| WO | WO 03/002109 | 1/2003 |
| WO | WO 2006/010283 | 2/2006 |
| WO | WO 2008/100539 | 8/2008 |
| WO | WO 2009/022327 | 2/2009 |
| WO | WO 2009/055729 | 4/2009 |
| WO | WO 2010/107404 | 9/2010 |
| WO | WO 2011/041462 | 4/2011 |
| WO | WO 2011/159821 | 12/2011 |
| WO | WO 2012/064301 | 5/2012 |
| WO | WO 2013/012199 | 1/2013 |
| WO | WO 2014/164282 | 10/2014 |

OTHER PUBLICATIONS

Borish MD, Larry, "Allergic Rhinitis: Systemic Inflammation and Implications for Management", The Journal of Allergy and Clinical Immunology, Dec. 1, 2003, pp. 1021-1031.

Ciebieada, MD et al., "Montelukast with Desloratadine or Levocetirizine for the Treatment of Persistent Allergic Rhinitis", Annals of Allergy, Asthma & Immunology, Nov. 2006, vol. 97, pp. 664-671.

Hong et al., "Urticaria and Angioedema", Cleveland Clinic—Center for Continuing Education, Aug. 2010, pp. 11.

Ingelsson et al., "Nationwide Cohort Study of the Leukotriene Receptor Antagonist Montelukast and Incident or Recurrent Cardiovascular Disease", Journal of Allergy and Clinical Immunology, Mar. 2012, vol. 129, No. 3, pp. 702-707.e2.

International Search Report and Written Opinion received in PCT Application No. PCT/US2014/021706, dated Jun. 20, 2014 in 7 pages.

International Preliminary Report on Patentability received in PCT Application No. PCT/US2014/021706, dated Sep. 24, 2015 in 6 pages.

Khoury, MD et al., "Effect of Montelukast on Bacterial Sinusitis in Allergic Mice", Annals of Allergy, Asthma & Immunology, Sep. 2006, vol. 97, No. 3, pp. 329-335.

Kurowski et al., "Montelukast Plus Cetirizine in the Prophylactic Treatment of Seasonal Allergic Rhinitis: Influence of Clinical Symptoms and Nasal Allergic Inflammation", Allergy, 2004, vol. 59, pp. 280-288.

May, B. Chandler, "A Proposed Model for the Treatment of Acute Inflammation", Mazatlán, Mexico, LXIV Conference of the Mexican College of Clinical Immunology and Allergy, May 29, 2010, pp. 3.

May, B. Chandler, "Contemporary Treatment of Influenza", Santa Barbara, CA, 25th Annual Infectious Disease Conference, Dec. 18, 2009, pp. 36.

Min et al., "Levocetirizine Inhibits Rhinovirus-Induced Bacterial Adhesion to Nasal Epithelial Cells Through Down-Regulation of Cell Adhesion Molecules", Annals of Allergy, Asthma and Immunology, 2012, vol. 108, pp. 44-48.

Moiz et al., "Formulation and Evaluation of Bilayered Tablets of Montelukast and Levocetrizine Dihydrocholoride Using Natural and Synthetic Polymers", International Journal of Drug Delivery 3, Jan. 2011, pp. 597-618.

Nederkoorn et al., "Preventive Antibiotics in Stroke Study: Rationale and Protocol for a Randomised Trial", International Journal of Stroke, Apr. 2011, vol. 6, pp. 159-163.

Parker, MD et al., "A 48 Year Old Man with Recurrent Sinusitis, 1 Year Later", JAMA, Clinical Crossroads Update, Jan. 24/31, 2001, vol. 285, No. 4, p. 462.

Peroni et al., "Combined Cetirizine-Montelukast Preventative Treatment for Food-Dependent Exercise-Induced Anaphylaxis", Annals of Allery, Asthma, & Immunology, Mar. 2010, vol. 104, pp. 272-273.

Schad et al., "Effect of Montelukast on Pro-inflammatory Cytokine Production During Naturally Acquired Viral Upper Respiratory Infections (vURIs) in Adults", Journal of Allergy and Clinical Immunology, Elsevier, Amsterdam, NL, Feb. 2008, vol. 121, No. 2, p. S74.

Taber's® Cyclopedic Medical Dictionary, "Trauma", 18th Edition, 1997, pp. 1988-1989.

Tang, Angela, "A Practical Guide to Anaphylaxis", America Family Physician, Oct. 1, 2013, vol. 68, No. 7, pp. 1325-1333.

Tillement et al., "Compared Pharmacological Characteristics in Humans of Racemic Cetirizine and Levocetirizine, Two Histamine $H_1$-Receptor Antagonists", Biochemical Pharmacology, 2003, pp. 1123-1126.

Tillie-Leblond et al., "Relation Between Inflammation and Symptoms in Asthma", Allergy, vol. 64, No. 3, Mar. 1, 2009, pp. 354-367.

Yu et al., "Montelukast, a Cysteinyl Leukotriene Receptor-1 Antagonist, Dose- and Time-Dependently Protects Against Focal Cerebral Ischemia in Mice", Pharmacology, Jan. 2005, vol. 73, No. 1, pp. 31-40.

Eccles, Ron, "Understanding the Symptoms of the Common Cold and Influenza", The Lancet Infectious Diseases, R(1) Nov. 2005, vol. 5, No. 11, pp. 718-725.

Kuna et al., "Two Phase II Randomized Trials on the CR Th2 Antagonist AZD1981 in Adults with Asthma", Drug Design, Development and Therapy, 2016, vol. 10, pp. 2759-2770.

Mathiesen et al., "On the Mechanism of Interaction of Potent Surmountable and Insurmountable Antagonists with the Prostaglandin D2 Receptor CRTH2", Molecular Pharmacology, 2006, vol. 69, No. 4, pp. 1441-1453.

Modrykamien, MD et al., "The Acute Respiratory Distress Syndrome", Proceedings (Baylor University Medical Center) 2015, vol. 28, No. 2, pp. 163-171.

"Prostaglandin DP2 receptor", Wikipedia, https://en.wikipedia.org/wiki/Prostaglandin_DP2_receptor, Aug. 25, 2017, pp. 9.

* cited by examiner

| Eye Opening | E |
|---|---|
| spontaneous | 4 |
| to speech | 3 |
| to pain | 2 |
| no response | 1 |
| Best Motor Response | M |
| To Verbal Command: | |
| obeys | 6 |
| To Painful Stimulus: | |
| localizes pain | 5 |
| flexion-withdrawal | 4 |
| flexion-abnormal | 3 |
| extension | 2 |
| no response | 1 |
| Best Verbal Response | V |
| oriented and converses | 5 |
| disoriented and converses | 4 |
| inappropriate words | 3 |
| incomprehensible sounds | 2 |
| no response | 1 |

FIG. 6

USE OF LEVOCETIRIZINE AND MONTELUKAST IN THE TREATMENT OF TRAUMATIC INJURY

CROSS-REFERENCE TO RELATED APPLICATIONS

This application is a continuation of U.S. patent application Ser. No. 14/831,469, filed Aug. 20, 2015, which is a continuation of International Application No. PCT/US2014/021706, filed Mar. 7, 2014, which claims the benefit of priority to U.S. Provisional Patent Application No. 61/780,336, filed Mar. 13, 2013. The foregoing applications are fully incorporated herein by reference in their entireties for all purposes.

BACKGROUND

Acute lung injury (ALI) and acute respiratory distress syndrome (ARDS) were defined by a panel of experts in 2011 (an initiative of the European Society of Intensive Care Medicine endorsed by the American Thoracic Society and the Society of Critical Care Medicine) as the Berlin Definition. Presently there are three stages: mild, moderate, and severe with an associated increased mortality and increased median duration of mechanical ventilation in survivors. As shown by the Berlin Definition of Acute Respiratory Distress Syndrome (Table VII), the categories of ARDS are based in part on the degree of hypoxemia determined by the ratio of PaO2/FiO2, where the PaO2 is the partial pressure of oxygen in arterial blood and the FiO2 is the fraction of inspired oxygen. Management of ARDS includes treatment of the underlying condition, mechanical or noninvasive ventilation, fluid and hemodynamic therapy, treatment of opportunistic infection, nutrition, and pharmacologic therapy. Currently there is no specific pharmacologic therapy for ALI/ARDS. Agents that have failed in large trials include in part, glucocorticoids, alprostadil, surfactant, ketoconazole, N-acetylcysteine, procysteine, lisofylline, and site-inactivated recombinant factor VIIa. Given the concern for the increased risk of nosocomial infection or critical illness polyneuropathy, as well as the lack of improvement in mortality, the routine use of glucocorticoids in ARDS is not recommended.

Hypoxic-ischemic brain injury is a general classification of brain injury which includes, in part, brain trauma, cardiac arrest, vascular catastrophe (hemorrhagic, thrombotic stroke), poisoning (such as carbon monoxide or drug overdose) and central nervous system infection. Improved techniques have resulted in greater numbers of patients surviving with variable degrees of brain injury. The evolution of hypothermic treatment has been particularly useful in improving neurologic morbidity and decreasing mortality in survivors of cardiac arrest and major brain trauma. The induction of mild to moderate hypothermia to a target temperature of 32-34° C. has improved the neurologic outcomes; however, refinement of existing protocols with validated studies are needed.

Supportive and preventive care measures remain the mainstay of therapy in all forms of hypoxic-ischemic brain injury. In additions to concerted efforts to restore the central nervous system to its pre jury state, clinicians are additionally focused on preventing nosocomial infection, providing adequate nutrition and providing adequate prophylaxis against venous thromboembolism, and gastric stress ulceration.

Severe traumatic brain injury is defined as head trauma associated with a GlasgowComa Scale (GCS) score of 3-8. Traditionally, steroids were used in high doses for the treatment of traumatic brain injury to decrease the swelling and edema cause by the primary injury (such as skull fracture, cerebral contusion, and hemorrhage). However, more recently, a consensus of opinion holds that high-dose steroids increase the risk of secondary infection, gastric ulceration, electrolyte imbalance, fluid retention, and steroid induced diabetes mellitus. Moreover, high-dose methylprednisolone in the treatment of patients with severe traumatic brain injury was recently considered a contraindication.

SUMMARY

Certain embodiments provide methods of treating traumatic injury or a symptom of traumatic injury in a patient in need thereof. In some embodiments, the method comprises administering an effective amount of a combination of levocetirizine and montelukast to the patient.

In some embodiments, a method of treating lung injuries and brain injuries in a patient in need thereof is disclosed. In some embodiments, the method comprises administering to the patient an effective amount of a combination of levocetirizine and montelukast.

In a variation, a method of treating a lung injury in a patient in need is disclosed. The method comprises administering to the patient an effective amount of a combination of levocetirizine and montelukast.

In another variation, a method of treating a symptom of a lung injury in a patient in need thereof is disclosed. The method comprises administering to the patient an effective amount of a combination of levocetirizine and montelukast.

In a variation, a method of treating a brain injury in a patient in need is disclosed. The method comprises administering to the patient an effective amount of a combination of levocetirizine and montelukast.

In another variation, a method of treating a symptom of a brain injury in a patient in need thereof is disclosed. The method comprises administering to the patient an effective amount of a combination of levocetirizine and montelukast.

Any of the method described above, or described elsewhere herein, can include one or more of the following features.

The combination of levocetirizine and montelukast may be administered at the onset of symptoms for any of the disclosed methods. In some cases, the symptoms could precede the overt clinical presentation depending upon the nature and extent of the disease process, by days, weeks, months or even years, e.g., headache preceding a major stroke.

The combination of levocetirizine and montelukast may be administered at the time of diagnosis for any of the disclosed methods.

The combination of levocetirizine and montelukast may be administered in a sequential manner for any of the disclosed methods.

The combination of levocetirizine and montelukast may be administered in a substantially simultaneous manner for any of the disclosed methods.

In some embodiments of the disclosed methods, an additional active agent may be administered. Additional active agents include, but are not limited to, the broad spectrum of antibiotics, antivirals, anti-parasitics, antifungals, vasopressors, diuretics, anticoagulants, anti-seizure medications, proton pump inhibitors, glucocorticoids, H2 receptor antagonists, anti-inflammatories and anti-neoplastic drugs, or combinations thereof. For example, the antibiotic can be vancomycin, meropenem, amoxicillin/beta clauvulanic acid, levofloxacin, piperacillin/tazobactam, ceftriaxone, clindamycin, azithromycin, trimethoprim/sulfamethoxazole, doxycycline or combinations thereof.

In some embodiments of the disclosed methods, the combination may be administered to the patient by one or more of the routes consisting of enteral, intravenous, intraperitoneal, inhalation, intramuscular, subcutaneous and oral.

In some embodiments, the levocetirizine and montelukast may be administered by the same route.

One embodiment is directed to methods, formulations and kits for treating acute lung or brain injuries. The methods and formulations include, but are not limited to, methods and formulations for delivering effective concentrations of levocetirizine and montelukast to a patient in need. The methods and formulations can comprise conventional and/or modified-release elements, providing for drug delivery to the patient.

In some embodiments, a combination of levocetirizine and montelukast, either as a single formulation or as separate formulations, may be administered as an emergency medication. For example, in some embodiments, a combination of levocetirizine and montelukast, either as a single formulation or as separate formulations, may be administered immediately at the onset of symptoms. In some embodiments, a combination of levocetirizine and montelukast, either as a single formulation or as separate formulations, may be administered substantially close to the onset of symptoms or at the time of diagnosis.

In some embodiments, the methods of treatment, formulations and kits may include e.g., a bilayer tablet, comprising levocetirizine and montelukast in separate layers, for daily administration. Alternatively, each medication may be administered separately (one tablet of levocetirizine and one tablet of montelukast per day in the evening). In some embodiments, a combination of levocetirizine and montelukast, either as a single formulation or as separate formulations, may be administered for 1, 2, 3, 4, 5, 6, 7, 8, 9, 10, 11, 12, 13, 14, or 15 days for the treatment of lung or brain injury. The bilayer tablets or the separate tablets may be packaged in a blister pack supplied for a 7 to 10 day course of therapy, with instructions including indications, administration instructions and precautions. In some embodiments, a combination of levocetirizine and montelukast, either as a single formulation, such as a bilayer tablet, or as separate formulations, may be administered for approximately 15, 20, 30, 60, 90 or more days or more for the treatment of lung or brain injury. Depending upon the nature and extent of the injuries, an extended treatment period may be required to clear blood from the perinasal sinuses and/or to foreshorten healing times, particularly in those patients undergoing multiple procedures during their hospitalization. The bilayer tablets or the separate tablets may be packaged in a blister pack supplied for a 30 day course of therapy, with instructions including indications, administration instructions and precautions. In some embodiments, the levocetirizine and montelukast, may be independently administered via nasogastric tube 1, 2, 3, 4, 5, 6, 7 or 8 times per day.

BRIEF DESCRIPTION OF THE DRAWINGS

FIG. 2A shows CT images taken of the chest of an eighteen year old male trauma patient presenting with brain, lung, facial, and liver injuries (See Example 1). FIG. 2A shows a CT image of the patient's chest with contrast, hospital day number 4; thirty six hours following the institution of levocetirizine plus montelukast. Failure to rapidly progress on the synergistically acting anti-inflammatory molecules lead to a bronchoscopy for removal of a retained foreign body (food). The patient was thereafter successfully extubated approximately 1.5 days later. FIG. 2B shows a montage image of the patient's brain without contrast, 72 hours following the injury and approximately 30 hours following initiation of levocetirizine plus montelukast. The cerebral edema has stabilized. Concurrently there has been a slight interval improvement in the patient's bilateral frontal lobe contusions.

FIG. 5A shows an image taken prior to the initiation of therapy, as the condition is worsening in the early morning hours following admission (moderate ARDS by the Berlin definition). FIG. 5B shows an image taken 8 days following injury and treatment with the combined medication, levocetirizine plus montelukast. The chest x-ray has cleared. The patient was extubated hospital day number 2 and discharged hospital day number 4. The mean intubation time for moderate ARDS as defined by the Berlin definition is 7 days.

FIG. 6 shows a diagram of the Glasgow Coma Scale (GCS). The GCS ranges from 3-15 and is an assessment tool used by emergency medical providers to objectively provide a degree of consciousness.

DETAILED DESCRIPTION

Figure 1:
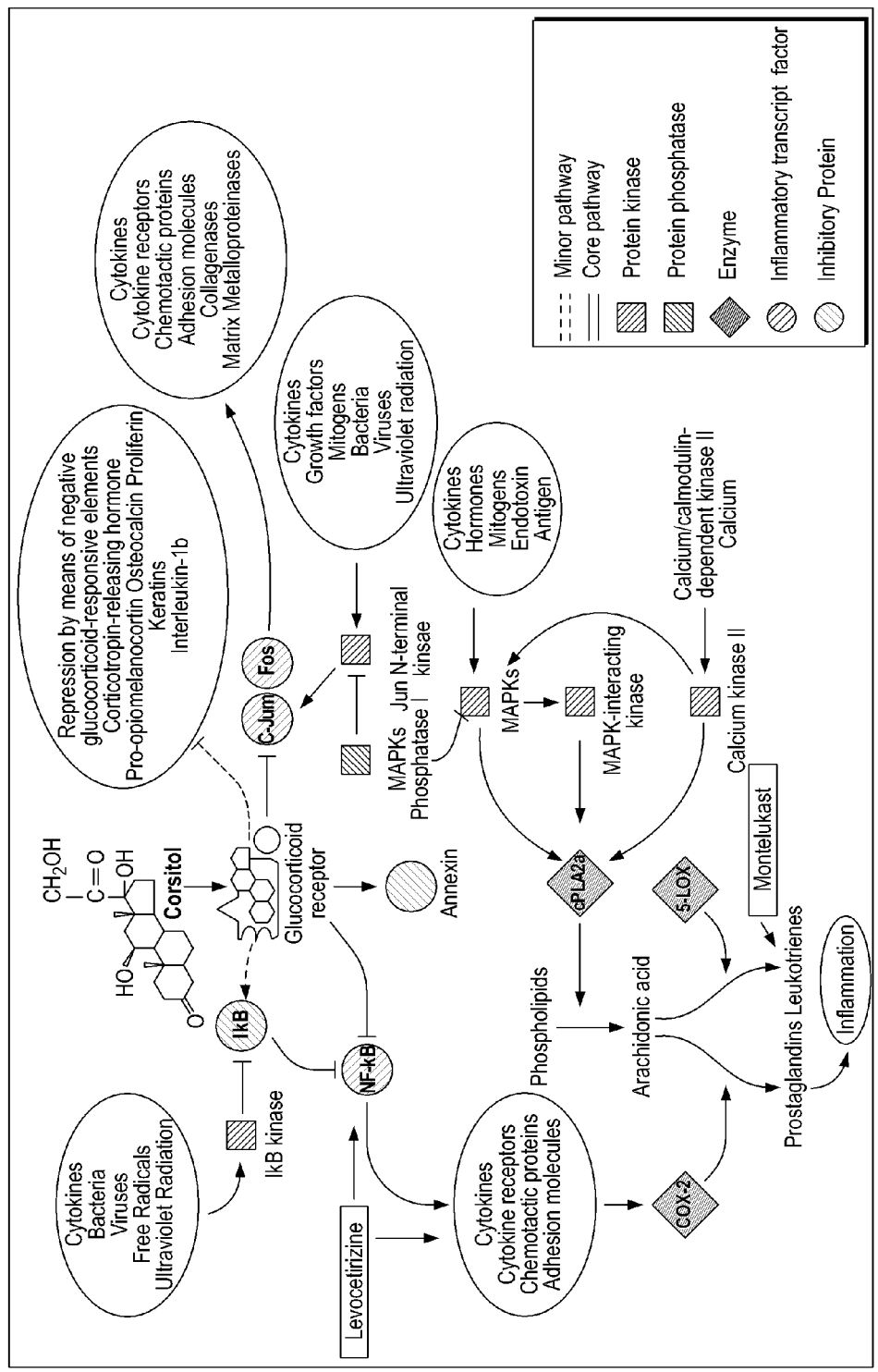
FIG. 1 shows a diagram of the proposed anti-inflammatory mechanism of action of levocetirizine and montelukast utilizing a steroid model pathway.

The present embodiments relate to the combination of levocetirizine and montelukast as a medicament for the treatment of acute, subacute and chronic inflammation. Several embodiments relate to the combination of levocetirizine and montelukast for the treatment of non-IgE-mediated, IgE-mediated, and/or combined non-IgE-mediated and IgE-mediated inflammation. Traditional allergic rhinitis is an IgE mediated disease; up to 70-80% of patients with asthma also have allergic rhinitis (atopic asthma). Administration of levocetirizine and montelukast in combination exhibits synergistic effects and unexpectedly superior results in the treatment of influenza, common cold, allergic rhinitis and acute, subacute, and chronic inflammation. Moreover, combinations of levocetirizine and montelukast can be used safely in conjunction with many existing treatment protocols.

Levocetirizine is an antihistamine and montelukast is a leukotriene receptor antagonist. As described herein, synergy between levocetirizine and montelukast shortens the course of the disease processes, thereby decreasing morbidity and mortality. This combined therapy also can improve quality of life from the amelioration of symptoms/side effects/disease process itself, and can decrease health-care costs. This synergistic effect can be observed in the use of a combination of levocetirizine and montelukast to treat non-IgE-mediated inflammation and combined non-IgE-mediated and IgE-mediated inflammation. Not wishing to be bound by a particular theory, the non-IgE-mediated response may be related, at least in part, to the fact that both levocetirizine and montelukast affect eosinophil migration, the leukocyte that is considered a hallmark of inflammation.

Levocetirizine, a potent H1-antihistamine, acts primarily by down-regulating the H1 receptor on the surface of mast cells and basophils to block the IgE-mediated release of histamine which cause the cardinal symptoms of allergic rhinitis: sneezing, rhinorrhea, nasal congestion, itchy palate and itchy red and watery eyes. Levocetirizine offers a short time to peak plasma level, 0.9 hr., a short time to steady state level, 40 hours, a low volume of distribution, 0.4 L/kg, and an enhanced receptor affinity of 5× over first generation mepyramine in an acidic pH (many acute inflammatory disease states are associated with acidosis, a low physiologic pH). Levocetirizine has a 24 hour receptor occupancy of ~75%, the highest of the commercially available antihistamines. Receptor occupancy of the second generation antihistamines appears to correlate with the pharmacodynamic activity in skin wheal and flare studies and with efficacy in allergen challenge chamber studies. Levocetirizine is approved in the US for the treatment of perennial allergic rhinitis and chronic idiopathic urticaria down to six months of age.

Levocetirizine has been objectively established as the most potent of the five modern generation antihistamines through histamine induced wheal and flare data. For example, levocetirizine at 5 mg per day is more effective than fexofenadine at its commonly prescribed dose of 180 mg per day in the United States. In Europe the adult dose is 120 mg per day. Levocetirizine has a lower volume of distribution, greater histamine receptor affinity in an inflamed state (low pH), and greater receptor occupancy at 24 hours at physiologic doses than fexofenadine. The corresponding values are shown in Table I.

TABLE I

COMPARISON BETWEEN FEXOFENADINE AND LEVOCETIRIZINE

|  | Fexofenadine | Levocetirizine |
| --- | --- | --- |
| Vd-L/kg | 5.6 L/kg | 0.4 L/kg |
| Receptor affinity in an acidic ph | increased 2× | increased 5× |
| Histamine receptor occupancy at 24 hours | ~25% | ~75% |
| Steady-state level | 3 days | 40 hours |

Levocetirizine decreases human rhinovirus titers in vitro by log-2. Not to be bound by a particular theory, the cellular mechanism of action is a proposed reduction of the activation of the intracellular protein complex NF-kB (nuclear factor kappa B) which is in turn responsible for the reduction of I-CAM-1. I-CAM-1, a transmembrane protein, is viewed as the portal of entry of human rhinovirus into the cell. Rhinovirus can be found in ~50% of cases of acute asthma and is responsible for 30-50% cases of the 'common cold.' A one-log reduction in viral titers has been independently determined to correlate with improved symptoms. In addition, levocetirizine has been shown to decrease eosinophil migration and decrease inflammatory mediators, IL-4, IL-6, and IL-8. IL-6, a signaling protein, regulates in part: fever, the body's response to trauma, and the acute (immediate) phase of the allergic reaction.

Montelukast, a leukotriene receptor antagonist, acts by binding with high affinity and selectivity to the CysLT1 receptor to inhibit the physiologic actions of the leukotriene LTD4. Leukotrienes are fatty signaling molecules whose effects include airway edema, smooth muscle contraction and altered cellular activity associated with the inflammatory process. Overproduction of leukotriene is a major cause of inflammation in asthma and allergic rhinitis. The cysteinyl leukotrienes (LTC4, LTD4, LDE4) are products of arachidonic acid metabolism. These leukotrienes are released from various cells including mast cells and eosinophils. They bind to receptors in the human airway and on other pro-inflammatory cells including eosinophils and certain myeloid stem cells. The cysteinyl leukotrienes have been correlated with the pathophysiology of asthma and allergic rhinitis.

Leukotriene $D_4$ is the most potent of the cysteinyl leukotrienes in contracting airway smooth muscle. Leukotriene receptors, such as $CysLT_1$, are found throughout the cells of the respiratory tree (including airway smooth muscle cells and airway macrophages) as well as on other pro-inflammatory cells in the body, particularly eosinophils and certain myeloid stem cells. Leukotrienes also function to promote the recruitment of eosinophils, dendritic cells and T cells. Eosinophil infiltration is considered by some authorities as a hallmark of inflammation.

Montelukast is FDA approved in the US for the treatment of perennial allergic rhinitis, asthma, seasonal allergic rhinitis, and exercised induced bronchospasm. Montelukast has been shown to be ineffective in improving asthma control or cold symptom scores caused by experimental rhinovirus infection. See Kloepfer K M, et al., Effects of montelukast in patients with asthma after experimental inoculation with human rhinovirus 16. Annals Allergy Asthma Immunology. 2011; 106:252-257. Unlike levocetirizine, no decrease in viral shedding was observed in rhinovirus-infected individuals treated with montelukast and there was no significant difference in reported cold symptom scores compared to placebo-treated individuals. Analysis of secondary outcomes suggests that montelukast may protect against reductions in lung function and increases in sputum eosinophils caused by common cold infections. During the recovery phase the percentage of sputum eosinophils was elevated in the placebo group, while the montelukast group remained at baseline levels. Further, peak expiratory flow was not decreased in the montelukast-treated patients. Other studies have shown that montelukast treatment has no effect on the respiratory symptoms of patients with acute respiratory syncitial virus bronchiolitis. See Bisgaard, H., et al., Study of montelukast for the treatment of respiratory symptoms of post-respiratory syncitial virus bronchiolitis in children, Am. J. Respir. Crit. Care Med., 2008; 178:854-860; and Proesmans, M., et al., Montelukast does not prevent reactive airway disease in young children hospitalized for RSV bronchiolitis, Acta Paediatr. 2009; 98:1830-34. However, some studies indicate that treatment with montelukast reduced the number of days with worsened asthma symptoms and unscheduled doctor's visits in children with mild allergic asthma and resulted in a modest reduction of symptoms in children with recurrent wheezing when given at the first sign of upper respiratory tract illness. See Sears, M. R. and Johnston, N. W., Understanding the September asthma epidemic. J. Allergy Clin. Immunol. 2007; 120:526-29; Bacharier, L. B., et al., Episodic use of an inhaled corticosteroid or leukotriene receptor antagonist in preschool children with moderate-to-severe intermittent wheezing. J. Allergy Clin. Immunol. 2008; 122:1127-35.

Montelukast reaches a steady state level, like the second generation antihistamine, levocetirizine, in less than two days. Unlike other currently available leukotriene modulators, zileuton and zafirlukast, routine monitoring of liver function tests is not required. There are no drug interactions with warfarin, theophylline, digoxin, terfenadine, oral contraceptives, or prednisone.

The two molecules are safe, i.e., FDA approved in the United States for allergic disorders down to age six months. They can be given primarily or in conjunction with many of the existing therapeutic protocols for the treatment of inflammation, including but not limited to, influenza, acute asthma and the common cold. Both medications are pregnancy category B (Table II).

TABLE II

PREGNANCY CATEGORY DEFINITIONS

| Category | Definition | Explanation |
|---|---|---|
| A | Generally acceptable | Controlled studies in pregnant women show no evidence of fetal risk. |
| B | May be acceptable | Either animal studies show no risk but human studies not available or animal showed minor risks and human studies were done and showed no risk. |
| C | Use with caution if benefits outweigh risks | Animal studies show risk and human studies not available or neither animal nor human studies were done. |
| D | Use in life-threatening emergencies when no safer drug is available | Positive evidence of human fetal risk. |
| X | Do not use in pregnancy | Risks involved outweigh potential benefits. Safer alternatives exist. |

Existing treatment of inflammation focuses on the underlying condition and nature of the presentation. Commonly employed are a myriad of agents such as: diphenhydramine (Benadryl®), oxygen, epinephrine, steroids, beta-agonists, non-steroidal anti-inflammatory agents (NSAIDS), antipyretics, antibiotics, antifungals, and antivirals. Paradoxically, the commonly employed NSAIDS actually increase the production of leukotrienes.

Steroids, which are widely used to treat inflammation, have significant short and long-term side-effects (Table III). With regard to treating inflammation associated with rhinosinusitis, nasal steroids have their limitations, particularly in the elderly and those patients on aspirin, clopidogrel or warfarin prescribed to reduce the risk of stroke and heart attack. Even in patients who do not take these traditional "blood thinners," the risk of spontaneous epistaxis from nasal steroid sprays is between 4-22%. The risk of epistaxis is medication dependent. Epistaxis is a significant consideration in many patients 55 or older.

TABLE III

STEROID SIDE EFFECTS

| Short term | Long term |
|---|---|
| Increased propensity for opportunistic infection | Glaucoma |
| | Cataracts |
| Increased blood pressure | High-blood pressure |
| Mood changes | Heart disease |
| Increased blood sugar | Diabetes mellitus |

TABLE III-continued

STEROID SIDE EFFECTS

| Short term | Long term |
|---|---|
| Increased intraocular pressure | Obesity |
| Water retention | Acid reflux/GERD |
| Weight gain | Osteoporosis |
| Increased risk for congestive heart failure | Myopathy |
| Flushing | Increased propensity for opportunistic infection |
| Increased appetite | |
| Insomnia | Cushing syndrome |

The typical daily dosage for levocetirizine is 5 mg for adults, and levocetirizine exhibits the following advantageous properties: i) Short time to reach peak plasma levels—0.9 hr; ii) Short time to steady state level—40 hrs; iii) Low volume of distribution (goes directly to the target receptor); iv) High receptor occupancy at 24 hours ~75%; v) Increased receptor affinity in inflamed tissue (acidic pH; up to 5× that of first generation molecules); vi) Pregnancy category B; vii) FDA approved down to six months for other disease states, i.e., perennial allergic rhinitis and chronic idiopathic urticaria; viii) Anti-inflammatory properties; and ix) Anti-viral properties. Studies in humans have shown that doses of levocetirizine up to 30 mg/day can be safely administered.

Montelukast, a leukotriene receptor antagonist, acts concurrently to protect the respiratory tree as well as block mediators in the inflammatory cascade. The typical daily dosage of montelukast is 10 mg for adults, and montelukast exhibits the following advantageous properties: i) montelukast is a selective receptor antagonist, inhibiting the physiologic action of $LTD_4$ at the $CysLT_1$ receptor; ii) montelukast binds with high affinity and selectivity to the $CysLT_1$ receptor without producing any agonist activity; iii) montelukast is rapidly absorbed; iv) montelukast reaches a peak plasma concentration in 3-4 hours; v) the oral bioavailability and C. of montelukast are not affected by a standard meal; vi) montelukast has a linear pharmacokinetics to 50 mg; vii) doses as low as 5 mg in adults cause substantial blockage of $LTD_4$-induced bronchoconstriction; viii) in a placebo controlled crossover study, montelukast inhibited early-phase bronchoconstriction due to antigen challenge by 75%; ix) montelukast is FDA approved down to six months of age; and x) montelukast has no drug interactions with warfarin, theophylline, digoxin, terfenadine, oral contraceptives, or prednisone. Montelukast has been administered at doses up to 200 mg/day to adult patients for 22 weeks and in short-term studies, and up to 900 mg/day to patients for approximately one week without clinically important adverse experiences.

Accordingly, both levocetirizine and montelukast are pregnancy category B in the United States and are FDA approved in the United States down to six months of age for other disease processes. Moreover, both drugs have only once daily dosing, and no routine monitoring of blood work is necessary for most clinical situations. Further, both drugs exhibit minimal clinically relevant interactions with other medications. As described herein, both levocetirizine and montelukast [administered orally] reach steady state levels within two days to rapidly produce a synergistic and complementary anti-inflammatory effect.

Administration of montelukast and a second generation antihistamine, fexofenadine, has a synergistic effect in the treatment of allergic rhinitis. Allergic rhinitis, also known as pollenosis or hay fever, is an allergic inflammation of the nasal airways which occurs when an allergen such as pollen or dust is inhaled by an individual with a genetically susceptible immune system (estimated at greater than 20 percent of the population). The allergen triggers antibody production, a serum specific immunoglobulin E (IgE), which in turn can bind to mast cells and basophils containing histamine. Upon re-exposure to the offending antigen, histamine is released causing the itching, swelling, and mucus production which are well known to seasonal allergy suffers. A combination of montelukast and fexofenadine reduced nasal congestion both subjectively, using patient diary and VAS evaluations, and objectively, using rhinomanometry and physical examination, with statistical significance compared to fexofenadine alone or fexofenadine with placebo.

However, the scientific literature does not clearly indicate whether the combination of an antihistamine plus a leukotriene offers an advantage over each alone for treatment in general. For example, in one chronic inflammatory disease state, chronic idiopathic urticaria, montelukast did not appear to offer an advantage over the second generation antihistamine desloratadine. See DiLorenzo G, et. al. Randomized placebo-controlled trial comparing desloratadine and montelukast in combined therapy for chronic idiopathic urticaria. J Allergy Clin Immunol 2004; 114-:619-25. Further, the FDA in April 2008 did approve the combination of loratadine, also a second generation antihistamine, and montelukast for the treatment of allergic rhinitis and asthma, finding no benefit from a combined pill.

Here, we describe the unexpected synergistic effects of combining levocetirizine and montelukast. Not wishing to be bound by a particular theory, a detailed examination of the pharmacokinetics of levocetirizine at the cell level illuminates the unique inflammatory properties that extend beyond the IgE mediated release of histamine. Levocetirizine exhibits a low volume of distribution (0.4 L/kg), prolonged dissolution time from the H1 receptor in an acidic pH, enhanced receptor affinity as a pure isomer of cetirizine, and the highest receptor occupancy at 24 hours of any currently available antihistamine. Such parameters impart an inflammatory effect by down regulating IL-4, IL-6, IL-8 as well as cellular adhesion molecules. The later are a homogeneous group of inducible immunoglobulins, integrins and selectins involved in cell-to-cell adhesion, cellular recruitment, homing and healing. In addition levocetirizine has been shown in vivo to decrease ICAM-1, IL-6, IL-8, TLR3 expression and NF-kappa B activation resulting in decreased human rhinovirus titers by log-2. Many rhinovirus serotypes share the same cellular receptor identifying ICAM-1 as the portal of entry into the cell. Levocetirizine inhibits rhinovirus-induced ICAM-1 and cytokine expression and viral replication in airway epithelial cells. One log reduction in viral shedding results in a significant clinical benefit in HRV-infected (human rhinovirus) patients.

An unmet clinical need arose in 2009 with the H1N1 pandemic. The primary drug of choice for influenza, oseltamivir, did not appear to reduce influenza related lower respiratory tract complications. For neuraminidase inhibitors, there was a shortening of the illness by only one half to one day, which indicated that neuraminidase inhibitors do not prevent infection or stop nasal viral excretion, and therefore may be a suboptimal means of interrupting viral spread in a pandemic. Moreover, during this time frame, California reported alarming data on the severity of H1N1 influenza in pregnant and postpartum women, i.e., from April 23 through Aug. 11, 2009, 22% of pregnant or postpartum women required intensive care for the treatment of H1N1 and 8% died. Clinically it was demonstrated that the combination of levocetirizine plus montelukast (the latter added to protect the lower airway; both of which were Pregnancy Category B), could be safely and effectively used to ameliorate/shorten the course of influenza.

Not wishing to be bound by a particular theory, the steroid model suggests that levocetirizine acts in a non-IgE-mediated capacity at the level of NF-kB (See FIG. 1) whereas montelukast acts at the CysLT1 receptor to inhibit the physiologic actions of LTD4. Both molecules are known to reduce the quantity of eosinophils or their migration to site of inflammation. Montelukast, in addition, also decreases the recruitment of dendritic cells and T cells.

The actions of levocetirizine plus montelukast surpass the individual physiologic mechanisms of each, well beyond the treatment of allergic rhinitis and asthma. At least in part, it is the anti-viral and anti-inflammatory properties of levocetirizine vis-a-vis nuclear factor kB; the inhibition of the actions of LTD4 by montelukast, underscored by ability of both levocetirizine and montelukast to inhibit the eosinophil quantity/migration, which impart synergy. This synergy is reflected by significantly improved clinical outcomes in a myriad of acute and chronic inflammatory disease states.

Embodiments described herein relate to methods of treating inflammation of the entire respiratory tree, including in part, the nose and paranasal sinuses known as rhinosinusitis with montelukast and levocetirizine. Rhinosinusitis considered on a timeline may be acute, with a duration of less than six weeks (usually 4-6 weeks), subacute, having a duration of six to twelve weeks, or chronic, having a duration of greater than or equal to twelve weeks. Acute rhinosinusitis may be precipitated by multiple factors not limited to chemical irritation, trauma, allergic rhinitis or an earlier upper respiratory tract infection, which may be bacterial, viral, or, less commonly, fungal in origin. The most common causative agents of acute sinusitis of bacterial origin are *Streptococcus pneumoniae, Haemophilus influenzae, Moraxella catarrhalis, Staphylococcus aureus*, other streptococci species, anaerobic bacteria, and, less commonly, gram negative bacteria. Bacterial sinusitis tends to be more persistent than viral rhinosinusitis, i.e., the common cold, which typically lasts for 7 to 10 days.

Several embodiments described herein relate to the treatment of acute rhinosinusitis caused by a viral or bacterial infection with montelukast and levocetirizine. In some embodiments, montelukast and levocetirizine are taken prophylactically to prevent a viral respiratory tract infection from escalating to an acute, often opportunistic, secondary bacterial sinusitis, bronchitis and/or pneumonia. In some embodiments, montelukast and levocetirizine are administered immediately, one hour, 6 hours, 12 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, and/or 30 days after exposure to the pathogens (virus, bacteria, fungi, etc.). Several embodiments relate to the treatment of patients with clinical manifestations of influenza with montelukast and levocetirizine. In some embodiments, montelukast and levocetirizine treatment reduces the duration of influenza. In some embodiments, montelukast and levocetirizine treatment reduces the severity of influenza symptoms. Several embodiments relate to the treatment of patients with clinical manifestations of the common cold with montelukast and levocetirizine. In some embodiments, montelukast and levocetirizine treatment reduces the duration of the cold. In some embodiments, montelukast and levocetirizine treatment reduces the severity of cold symptoms.

Chronic rhinosinusitis is an inflammatory condition/disease of the nose and paranasal sinuses lasting for greater than or equal to twelve weeks. Symptoms include in part, any combination of nasal congestion, facial pain, headache, coughing, an increase in asthma symptoms, malaise, discharge, feeling of facial tightness, dizziness, and/or aching teeth. Rhinosinusitis in general can be categorized into four categories: (1) acute bacterial rhinosinusitis (ABRS), (2) chronic rhinosinusitis without nasal polyposis (CRSsNP), (3) chronic sinusitis with nasal polyposis (CRSwNP), and (4) allergic fungal rhinosinusitis (AFRS). See Meltzer, E O. Rhinosinusitis: Developing guidance for clinical trials. J Allergy Clin Immunol 2006 November; S20. Nasal polyposis is a subgroup of chronic rhinosinusitis in which the inflammation of the nose is associated with two or more of the following signs and symptoms: nasal obstruction or congestion, nasal discharge, hyposmia or anosmia, facial pain or feeling of pressure, endoscopic evidence of polyps or mucopurulent discharge from middle meatus with or without edema or mucosal obstruction of the meatus and CT images which show mucosal changes of osteomeatal complex or paranasal sinuses. See Fokkens W, et. al. EAACI position paper on rhinosinusitis and nasal polyps executive summary. Allergy, 2005; 60, 583-601., Fokkens, W, et. al. European Position Paper on Rhinosinusitis and Nasal Polyps group (2007) European position paper on rhinosinusitis and nasal polyps. Rhinology 2007; 20, 1-136. Conventional treatment for chronic rhinosinusitis often involves functional endoscopic sinus surgery, antibiotics, systemic and topical steroids, and to a much lesser extent an antihistamine or leukotriene modulator. The use of antihistamines in patients with only polyps has not been extensively studied. See Casale M, et. al. Nasal Polyposis: From Pathogenesis to Treatment, an Update. Inflammation & Allergy—Drug Targets 2011, 10, 158-163. Mometasone furoate monohydrate, a topical nasal steroid spray, is the only FDA approved medication in the United States for the treatment of nasal polyposis. The recommended dose is two squirts each nostril twice a day.

Embodiments described herein relate to the treatment of chronic rhinosinusitis with montelukast and levocetirizine. Several embodiments described herein relate to the treatment of nasal polyposis with montelukast and levocetirizine. In some embodiments, montelukast and levocetirizine treatment reduces the size and/or number of polyps. Some embodiments relate to the treatment of chronic rhinosinusitis with montelukast and levocetirizine in the absence of steroids, antibiotics or surgical treatment. In other embodiments, montelukast and levocetirizine are administered in conjunction with antibiotics and/or steroids and/or surgical treatment as deemed clinically applicable. The chronic rhinosinusitis treatment protocol with or without other treatment modalities is shown in Table IV.

TABLE IV

TREATMENT PROTOCOL FOR CHRONIC RHINOSINUSITIS

| Levocetirizine - U.S. | |
|---|---|
| Adults: | 5 mg/day |
| Children: 6-11 years of age: | 2.5 mg/day |
| Children: 6 months to 5 years | 1.25 mg/day |
| Montelukast - U.S. | |
| Adults: | 10 mg orally/day |
| Children 6-14 years of age: | 5 mg orally/day |
| Children 6 months-5 years of age: | 4 mg orally/day |

Patients may be seen at least quarterly in the office with endoscopic review of the nose/paranasal sinuses when clinically appropriate. A pretreatment and follow-up CT scan of the perinasal sinuses at 6 months to one year post initiation of therapy may be performed to provide objective data on which to tailor existing medical therapy.

Several embodiments relate to a method of treating rhinitis with montelukast and levocetirizine. Rhinitis, inflammation of the nasal passages, is commonly caused by a viral or bacterial infection, including the common cold, the latter of which is caused primarily by Rhinoviruses and Coronaviruses. See Eccles R. Understanding the Symptoms of the Common Cold and Influenza. Lancet Infectious Diseases 2005; 5(11): 718-725. Rhinitis is categorized as: (i) infective rhinitis; (ii) nonallergic rhinitis; and (iii) allergic rhinitis. Several embodiments relate to a method of treating infective rhinitis with montelukast and levocetirizine. Some embodiments relate to a method of treating nonallergic rhinitis with montelukast and levocetirizine. Some embodiments relate to a method of treating allergic rhinitis with montelukast and levocetirizine.

Several embodiments described herein relate to the treatment of chronic rhinosinusitis with montelukast and levocetirizine. Some embodiments, relate to the treatment of chronic rhinosinusitis with montelukast and levocetirizine in the absence of steroid or antibiotic treatment. In other embodiments, montelukast and levocetirizine are administered in conjunction with antibiotics and/or steroids.

Several embodiments relate to a method of treating non-IgE-based inflammation with montelukast and levocetirizine.

Several embodiments relate to a method of treating combined IgE and non-IgE-mediated inflammation with montelukast and levocetirizine.

Table V shows the existing U.S. national guidelines for dosages in the treatment of allergic disorders.

TABLE V

GUIDELINES FOR DOSAGES IN THE TREATMENT OF ALLERGIC DISORDERS

| Levocetirizine - U.S. | |
|---|---|
| Adults: | 5 mg/day |
| Children: 6-11 years of age: | 2.5 mg/day |
| Children: 6 months to 5 years | 1.25 mg/day |
| Montelukast - U.S. | |
| Adults: | 10 mg orally/day |
| Children 6-14 years of age: | 5 mg orally/day |
| Children 6 months-5 years of age: | 4 mg orally/day |

Several embodiments relate to the use of a combination of levocetirizine and montelukast to treat a bacterial infection. Examples of bacterial infections that may be treated by a combination of levocetirizine and montelukast include, but are not limited to, acute bacterial rhinosinusitis (ABRS). In some embodiments, levocetirizine and montelukast may be administered with an antibiotic as determined by local presentation.

Several embodiments relate to the use of a combination of levocetirizine and montelukast to treat otitis media with effusion and associated ear disorders such as chronic mastoiditis and eustachian tube dysfunction (the auditory tube leading from the back of the nose to the middle ear). In some embodiments, levocetirizine and montelukast may be administered with antibiotics to treat for example, acute otitis media with purulent middle ear effusion. In some embodiments, levocetirizine and montelukast may be administered without antibiotics to treat chronic middle ear effusion, for example, chronic otitis media. In some embodiments, levocetirizine and montelukast may be administered with other treatment modalities such as, but not limited to, steroids and/or antiviral agents.

Several embodiments relate to the use of a combination of levocetirizine and montelukast to treat allergic fungal rhinosinusitis (AFRS). In some embodiments, levocetirizine and montelukast may be administered with other treatment modalities such as, but not limited to, steroids and/or an antifungal agent.

Intravenous therapy of levocetirizine and montelukast, the latter currently under investigation in the United States, would enhance the individual and combined clinical response presently seen with the administration of oral medication. The IV montelukast plasma concentration area under the curve profile, 7 mg, is comparable to the approved 10 mg oral montelukast tablet. The former has been shown in acute asthmatics to significantly improve FEV1 (forced expiratory volume at one sec) at 10 minutes when compared with placebo.

Accordingly, the dosing for acute inflammation could be daily as delineated above individually in the same setting, as a dual-layer tablet(s), and/or as a blister pack containing both medications for a 10 day course of therapy. For a moderate to severe clinical presentation, the levocetirizine component can be given at time zero (5 mg), 12 hours (5 mg) and 24 hours (5 mg), during the first 24 hour day, in order to achieve a steady state level of the molecule in less than 40 hours. Levocetirizine human dosing safety studies have been performed at up to 30 mg/day. Sedation is the principal side effect experienced at higher doses. Independent research has shown that levocetirizine alone can be dosed at 20 mg/day to treat severe cases of idiopathic urticaria.

The application for the combination of levocetirizine and montelukast includes, but is not limited to treating, ameliorating, or preventing the following symptoms. For influenza, the combination can be useful to shorten the course of seasonal flu and prevent or minimize the development of lower respiratory tract infections/complications, and/or to establish an improved, safe, world-wide protocol for influenza prior to the next pandemic, e.g., H5N1 with its associated 50% mortality rate. For upper respiratory tract infections, not limited to rhinovirus, the combination can be useful to limit the infection itself, and/or to prevent or reduce the potential development of secondary sinusitis, bronchitis and pneumonia. The combination can be useful for treatment of Ebstein-Barr Virus, particularly, but not limited to those patients with respiratory involvement.

For acute asthma in conjunction with existing protocols, not limited to exacerbations caused by rhinovirus (~50% of cases), the combination can be useful to shorten the course of the event, reduce hospitalizations and death. The combination can be useful for pre-treatment of patients allergic to one or more classes of antibiotics requiring antimicrobial therapy. These patients are at risk, 4-10× over the general population, of developing a subsequent ALE (allergic-like event). For patients with moderate to severe life-threatening disease requiring dual/triple antibiotics, the combination can be useful to reduce the probability of developing a side-effect(s) from the primary treatment medications. The combination can be useful during and following radiation therapy to ameliorate the inflammatory response. The combination can be useful for patients requiring steroids for the treatment of inflammation who are otherwise at increased risk for the development of steroid induced complications. Examples include but are not limited to the following: i) A severe insulin dependent diabetic with an infection such as facial paralysis, and ii) Patient with latent Tuberculosis. For patients on antiviral medication for acute disease, the combination can be used to prevent complications related to the medication(s) as well as complications associated with the disease process itself. The combination can be used to treat serum sickness, with or without steroids. For pre-treatment of patients on immunotherapy, the combination can be used to prevent or ameliorate the risk of a systemic reaction. Examples of high risk patients with the potential to develop a life-threatening, systemic event include but are not limited to severe asthmatics, those patients with a concurrent respiratory tract infection, and those patients with a prior history of a systemic reaction. For pre and intra-treatment of those patients on chemotherapy, the combination can be used to ameliorate side effects associated with the administration of chemotherapeutic drug(s). For patients exhibiting a transfusion reaction, the combination can be used to limit the side effects/life threatening event during the initial reaction and in preparation for any requisite subsequent transfusion.

As will be readily apparent to one skilled in the art, the useful in vivo dosage of levocetirizine and montelukast to be administered and the particular mode of administration will vary depending upon the age, weight, medical condition of the patient, the severity of the condition to be treated, the route of administration, the renal and hepatic function of the patient, and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Advantageously, compounds of the present embodiments may be administered, for example, in a single daily dose, or the total daily dosage may be administered in divided doses of two, three or four times daily.

TABLE VI

TREATMENT PROTOCOL FOR ACUTE INFLAMMATION NOT LIMITED TO INFLUENZA AND THE COMMON COLD

| Levocetirizine - U.S. | |
| --- | --- |
| Adults: | 5 mg/day |
| Children: 6-11 years of age: | 2.5 mg/day |
| Children: 6 months to 5 years | 1.25 mg/day |
| Montelukast - U.S. | |
| Adults: | 10 mg orally/day |
| Children 6-14 years of age: | 5 mg orally/day |
| Children 6 months-5 years of age: | 4 mg orally/day |

Depending upon the severity of the acute process, the doses in Table VI can be modified. For example, the age appropriate dose for levocetirizine may be given at time zero (at presentation) with an additional age appropriate dose at 12 hours. In order to protect the lower airway, particularly in the face of bronchitis/pneumonia, a dose of montelukast may be given at time zero (at presentation) with an additional age appropriate dose of montelukast at 12 hours. In this fashion the steady state level of the two drugs would approach 24 hours. Montelukast, like levocetirizine, is considered a very safe molecule. Montelukast has been administered at doses up to 200 mg/day (20× the standard adult daily dose) to adult patients for 22 weeks and in short-term studies, up to 900 mg/day (90× the standard adult daily dose) to patients for approximately one week without clinically important adverse events. Dosing duration may parallel the generally accepted protocols for their respective disease states. For example, conventional therapy for an acute infectious disease process is typically administered for 5-14 days. A course of combined levocetirizine once daily plus montelukast once daily may be given for the same duration. For the treatment of chronic inflammatory disease states, an age appropriate once daily dosing of each medication may also be administered.

Brain Injuries

Hypoxic-ischemic brain injury is a general classification of brain injury which includes in part, brain trauma, cardiac arrest, vascular catastrophe (hemorrhagic, thrombotic stroke), and poisoning (such as carbon monoxide or drug overdose) and central nervous system infection. Improved techniques have resulted in greater numbers of patients surviving with variable degrees of brain injury. The evolution of hypothermic treatment has been particularly useful in improving neurologic morbidity and decreasing mortality in survivors of cardiac arrest and major brain trauma. The induction of mild to moderate hypothermia to a target temperature of 32-34° C. has improved the neurologic outcomes; however, refinement of existing protocols with validated studies are needed.

Supportive and preventive care measures remain the mainstay of therapy in all forms of hypoxic-ischemic brain injury. In additions to concerted efforts to restore the central nervous system to its pre jury state, clinicians are additionally focused on preventing nosocomial infection, providing adequate nutrition and providing adequate prophylaxis against venous thromboembolism, and gastric stress ulceration.

Severe traumatic brain injury is defined as head trauma associated with a Glasgow Coma Scale (GCS) score of 3-8. The GCS ranges from 3-15 and is an assessment tool used by emergency medical providers to objectively provide a degree of consciousness. The following equation is used: $E+M+V=3$ to $15$; FIG. 6 provides a definition for each of these variables. A GCS score greater than or equal to 9 typically indicates that a patient is not in coma. More specifically, a score of 9-11 indicates moderate severity, and a score greater than or equal to 12 indicates a minor injury. A GCS score of 8 is thus a critical score: 50% of patients with a GCS score of less than or equal to 8 at 6 hours die and 90% of patients with a GCS score of less than or equal to 8 are in coma.

The estimated cost of treatment for all categories of traumatic brain injury (TBI) is $80 billion per year. TBI is the leading cause of mortality for Americans between the age of one and forty-five years. Over the past two decades guidelines have evolved to improve injury outcomes particularly those endorsed by the World Health Organization Committee in Neurotramatology.

From the contemporary literature, it can be found that traumatic brain injury is divided into two distinct periods: primary and secondary. The primary brain injury is the physical damage to the parenchyma (tissue, vessels) that occurs during the traumatic event, e.g., skull fracture, cerebral contusion and hemorrhage.

The secondary injury is the result of a complex process that occurs over the ensuing hours to days. Numerous secondary brain insults may occur as the result of intracranial, extracranial, and systemic therapy or the lack thereof. Secondary brain insults, mainly ischemic in nature, include in part, cerebral edema, hematomas, hydrocephalus, intracranial hypertension, vasospasm, metabolic derangement, excitotoxicity, calcium ions toxicity, infection, and seizures. Other disorders (for example, bacterial meningitis) can also involve secondary ischemia and thus neuronal injury.

Traditionally, steroids were used in high doses (for example, 24 mg dexamethasone in 24 hours) for the treatment of traumatic brain injury to decrease the swelling and edema cause by the primary injury (such as skull fracture, cerebral contusion, and hemorrhage). Steroids were effective, at least in part, in ameliorating the posttraumatic ischemia associated with the release of oxygen free radicals, excitatory amino acids, cytokines and other inflammatory mediators. In May 2004, a CRASH study published data on 10,008 patients that showed the risk of death from all causes within 2 weeks of traumatic brain injury was higher in the steroid versus placebo groups (21.1% and 17.9%, respectively). Although the rise in risk of death was unclear, a consensus of opinion holds that high-dose steroids increase the risk of secondary infection, gastric ulceration, electrolyte imbalance, fluid retention, and steroid induced diabetes mellitus. Recent guidelines published by Bullock R. J Neurotrauma. 3. Supple 1. Vol. 24. 2007, pp. S1-S106, herein incorporated by reference in its entirety, have stated that high-dose methylprednisolone in the treatment of patients with severe traumatic brain injury is contraindicated.

In addition, use of glucocorticoids for the treatment of secondary ischemia related to, for example, bacterial meningitis, has been controversial. However, some studies have reported that adults receiving dexamethasone for the treatment of bacterial meningitis had a lower percentage of unfavorable outcomes, including death, as compared to subjects who received placebo; in a study of pediatric patients, patients receiving dexamethasone also showed a reduction of meningeal inflammation and decreased audiologic and neurologic sequelae as compared to patients who received placebo. Moreover, patients treated with steroids for hemophilus influenza Type B infections have less long-term hearing loss than patients treated with antibiotics alone. However, dexamethasone can also decrease antibiotic penetration into the central nervous system, and thus the use of steroids can impede eradication of highly resistant bacterial strains from the cerebral spinal fluid and aggravate neuronal damage in the hippocampal formation.

The administration of levocetirizine and montelukast in combination exhibits synergistic effects and unexpectedly superior results in the treatment of brain injuries, particularly traumatic brain injuries. Without being bound to a particularly theory, levocetirizine and montelukast work to block the H1 and leukotriene receptors, respectively. Thus, levocetirizine and montelukast quickly block the release of histamine to reduce systemic swelling and improved lung function by inhibiting the release of leukotrienes. Furthermore, levocetirizine and montelukast combination synergistically decrease eosinophil (the white blood cell considered the hallmark of inflammation) migration and quantity. Moreover, levocetirizine blocks IL-6 (Interleukin 6). As a signaling protein, IL-6 is one of the most important mediators of the acute phase reaction to injury and fever. Importantly, IL-6 is capable of crossing the blood-brain brain barrier, which makes it a significant cytokine even in the presence of a less severe, closed head injury.

Autopsy specimens gleaned from the lungs of patients who have died from ARDS, both primarily and secondarily from their trauma, are underscored by the presence of neutrophils. Levocetirzine additionally blocks IL-8 (Interleukin 8), the signaling protein responsible for chemotaxis in target cells, primarily neutrophils, causing them to migrate to the site of injury. In addition to neutrophils there are a wide range of other cells, e.g., endothelial cells, mast cells, macrophages, and keritinocytes that respond to IL-8 as well. Thus, the combination of levocetirizine and montelukast is expected to decrease morbidity and mortality in patients suffering from traumatic brain injury, increase resolution of infection and enhance long-term neurological outcomes.

Advantageously, the use of steroids can be avoided. As discussed further in Example 1, the combination of levocetirizine and montelukast can also enhance a patient's clinical response (foreshortened healing time) following the addition of the combination of levocetirizine and montelukast to an acute brain trauma protocol. Thus, the combinations of levocetirizine and montelukast can be used safely in conjunction with many existing treatment protocols (e.g., acute brain injury, acute lung injury, acute stroke, meningitis, pneumonia, sepsis). For example, typical antibiotics can be administered to a patient in combination with levocetirizine and montelukast; such antibiotics include but are not limited to vancomycin, meropenem, amoxicillin/beta clauvulanic acid, levofloxacin, piperacillin/tazobactam, ceftriaxone, clindamycin, azithromycin, trimethoprim/sulfamethoxazole, doxycycline or combinations thereof. Additional agents also include, but are not limited to, the broad spectrum of antibiotics, antivirals, anti-parasitics and antifungals. Moreover, given the excellent safety profiles of both levocetirizine and montelukast, the combination can be administered with many common classes of medications used in an intensive care, hospital or outpatient setting, including but not limited to the vasopressors, diuretics, anticoagulants, anti-seizure medications, proton pump inhibitors, glucocorticoids (if necessary), H2 receptor antagonists, antipyretic agents, anti-inflammatories and anti-neoplastic drugs. There are very few acute/critical care medications that would pose a major treatment problem (e.g. significant drug interaction) other than a dose adjustment to allow for underlying liver or kidney failure.

The combination of levocetirizine and montelukast may be administered to the patient by one or more of the routes, such as enteral, intraperitoneal, inhalation, intramuscular, subcutaneous and oral. Furthermore, the combination of levocetirizine and montelukast may be administered intravenously, for example, to quickly deliver the combination as a dual emergency medication, thereby eliciting an even more robust response.

As will be readily apparent to one skilled in the art, the useful in vivo dosage of levocetirizine and montelukast to be administered and the particular mode of administration will vary depending upon the age, weight, medical condition of the patient, the severity of the condition to be treated, the route of administration, the renal and hepatic function of the patient, and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Advantageously, compounds of the present embodiments may be administered, for example, in a single daily dose, or the total daily dosage may be administered in divided doses of two, three or four times daily.

Lung Injuries

Acute lung injury (ALI) and acute respiratory distress syndrome (ARDS) were defined by a panel of experts in 2011 (an initiative of the European Society of Intensive Care Medicine endorsed by the American Thoracic Society and the Society of Critical Care Medicine) as the Berlin Definition. Presently there are three stages: mild, moderate, and severe with an associated increased mortality (27%; 95% CI, 24%-30%; 32%; 95% CI, 29%-34%; and 45%; 95% CI, 42%-48%, respectively; P<0.001) and increased median duration of mechanical ventilation in survivors (5 days; interquartile [IQR], 2-11; 7 days; IQR, 4-14; and 9 days; IQR, 5-17, respectively; P<0.001). The definition was empirically evaluated using patient-level meta-analysis of 4188 patients with ARDS from 4 multicenter clinical data sets and 269 patients with ARDS from 3 single-center data sets containing physiologic information. The categories of ARDS are based on the degree of hypoxemia determined by the ratio of PaO2/FiO2 where the PaO2 is the partial pressure of oxygen in arterial blood and the FiO2 is the fraction of inspired oxygen. In particular, the categorization is as follows: (1) Mild ARDS: 200 mm Hg<PaO2/FiO2 and less than or equal to 300 mm Hg; (2) Moderate ARDS: 100 mm Hg<PaO2/FiO2 and less than or equal to ≤200 mm Hg; and (3) Severe ARDS: PaO2/FiO2 is less than or equal to 100 mm Hg. Table VII shows the complete Berlin Definition of Acute Respiratory Distress Syndrome.

TABLE VII

BERLIN DEFINITION OF
ACUTE RESPIRATORY DISTRESS SYNDROME

Acute Respiratory Distress Syndrome

| | |
|---|---|
| Timing | Within 1 week of a known clinical insult or new or worsening respiratory symptoms |
| Chest imaging[a] | Bilateral opacities-not fully explained by effusions, lobar/lung collapse, or nodules |
| Origin of edema | Respiratory failure not fully explained by cardiac failure or fluid overload |
| | Need objective assessment (eg, echocardiography) to exclude hydrostatic edema if no risk factor present |
| Oxygenation[b] | |
| Mild | 200 mmHg < PaO$_2$/FIO$_2$ ≤300 mmHg with PEEP or CPAP ≥5 cm H$_2$O[c] |
| Moderate | 100 mmHg < PaO$_2$/FIO$_2$ ≤200 mmHg with PEEP ≥5 cm H$_2$O |
| Severe | PaO$_2$/FIO$_2$ ≤100 mmHg with PEEP ≥5 cm H$_2$O |

Abbreviations:
CPAP, continuous positive airway pressure;
FIO$_2$, fraction of inspired oxygen;
PaO$_2$, partial pressure of arterial oxygen;
PEEP, positive end-expiratory pressure.
[a]Chest radiograph or computed tomography scan.
[b]If altitude is higher than 1000 m, the correction factor should be calculated as follows: [PaO$_2$/FIO$_2$ x (barometric pressure/760)].
[c]This may be delivered noninvasively in the mild acute respiratory distress syndrome group.

Data suggest that this common ICU problem complicating a spectrum of critical illnesses is an estimated 190,000 cases in the United States per year. Whereas healthy lungs regulate the fluid to maintain a small amount of interstitial fluid and dry alveoli, lung injury causes excess fluid in both the interstitium and alveoli. The consequences of injury include in part, impaired gas exchange, decreased lung compliance, and increased pulmonary arterial pressure.

The causes of ARDS have been enumerated at more than 60 with the most common being: sepsis, aspiration, pneumonia, severe trauma (bilateral lung contusion, fat embolism after long bone fracture, sepsis that develops several days after severe trauma or burns, and massive traumatic tissue injury), massive transfusion, transfusion related acute lung injury, lung and hematopoietic stem cell transplantation, drugs and alcohol, and genetic determinants such as mutations in the surfactant protein B (SP-B) gene.

The pathophysiology is complex and remains incompletely understood. Neutrophils play an important role in the initial inflammatory response. Early ALI/ARDS is characterized by migration of neutrophils into the alveolar compartment which in turn release injurious substances such a proteases and gelatinases A and B.

Clinically the acute phase is depicted by the onset of radiographic infiltrates, consistent with pulmonary edema, hypoxemia and increased work of breathing. A late phase apparent after seven to 10 days is characterized by fibrosing alveolitis. Radiographically, linear opacities develop underscored by airspaces filled with granulation tissue. Characteristically there is a need for continued mechanical ventilation with high levels of PEEP (positive end expiratory pressure) and high levels of inspired oxygen (FiO2).

Management of ARDS (Table VIII) includes treatment of the underlying condition, mechanical or noninvasive ventilation, fluid and hemodynamic therapy, treatment of opportunistic infection, nutrition, and pharmacologic therapy. Currently there is no specific pharmacologic therapy for ALI/ARDS. Agents that have failed in large trials include in part, glucocorticoids, alprostadil, surfactant, ketoconazole, N-acetylcysteine, procysteine, lisofylline, and site-inactivated recombinant factor VIIa. Given the concern for the increased risk of nosocomial infection or critical illness polyneuropathy, as well as the lack of improvement in mortality, the routine use of glucocorticoids in ARDS is not recommended.

TABLE VIII

MANAGEMENT OF PATIENTS WITH ARDS

| | |
|---|---|
| Calculate Predicted Body Weight (PBW) | Males: PBW (kg) = 50 + 2.3[(height in inches) − 60] or 50 + 0.91[(height in cm) − 152.4]. <br> Females: IBW (kg) = 45.5 + 2.3[(height in inches) − 60] or 45.5 + 0.91[(height in cm) − 152.4]. |
| Ventilator Mode | Volume assist/control until weaning. |
| Tidal Volume (VT) | Initial VT: 6 mL/kg predicted body weight. <br> Measure inspiratory plateau pressure (Pplat, 0.5 sec inspiratory pause) every 4 hours AND after each change in PEEP or VT. <br> If Pplat >30 cm $H_2O$, decrease VT to 5 or to 4 mL/kg. <br> If Pplat <25 cm $H_2O$ and VT <6 mL/kg PBW, increase VT by 1 ml/kg PBW. |
| Respiratory Rate (RR) | With initial change in VT, adjust RR to maintain minute ventilation. <br> Make subsequent adjustments to RR to maintain pH 7.30-7.45, but do not exceed RR = 35/min, and do not increase set rate if $Paco_2$ <25 mm Hg. |
| I:E Ratio | Acceptable range = 1:1 to 1:3 (no inverse ratio). |
| $FIO_2$, Positive End-Expiratory Pressure (PEEP), and Arterial Oxygenation | Maintain $Pao_2$ = 55-80 mm Hg or $Spo_2$ = 88%-95% using the following PEEP/$FIO_2$ combinations: <br> $FIO_2$  0.3-0.4  0.4  0.5  0.6  0.7  0.8  0.9  1 <br> PEEP    5-8     8-14 8-16 10-20 10-20 14-22 16-22 18-25 |
| Acidosis Management | If pH <7.30, increase RR until pH ≥7.30 or RR = 35/min. <br> If pH remains <7.30 with RR = 35, bicarbonate consider bicarbonate infusion. <br> If pH <7.15, VT may be increased (Pplat may exceed 30 cm $H_2O$). |
| Alkalosis Management | If pH >7.45 and patient not triggering ventilator, decrease set RR but not below 6/min. |
| Fluid Management | Once patients are out of shock, adopt a conservative fluid management strategy. <br> Use diuretics or fluids to target a central venous pressure (CVP) of <4 or a pulmonary artery occlusion pressure (PAOP) of <8. |
| Liberation from Mechanical Ventilation | Daily interruption of sedation. <br> Daily screen for spontaneous breathing trial (SBT). <br> SBT when all of the following criteria are present: <br> (a) $FIO_2$ <0.40 and PEEP <8 cm $H_2O$. <br> (b) Not receiving neuromuscular blocking agents. <br> (c) Patient awake and following commands. <br> (d) Systolic arterial pressure >90 mm Hg without vasopressor support. <br> (e) Tracheal secretions are minimal, and the patient has a good cough and gag reflex. |
| Spontaneous Breathing Trial | Place patient on 5 mm Hg pressure support with 5 mm Hg PEEP or T-piece. <br> Monitor HR, RR, oxygen saturation for 30-90 minutes. <br> Extubate if there are no signs of distress (tachycardia, tachypnea, agitation, hypoxia, diaphoresis). |

Figure 7:
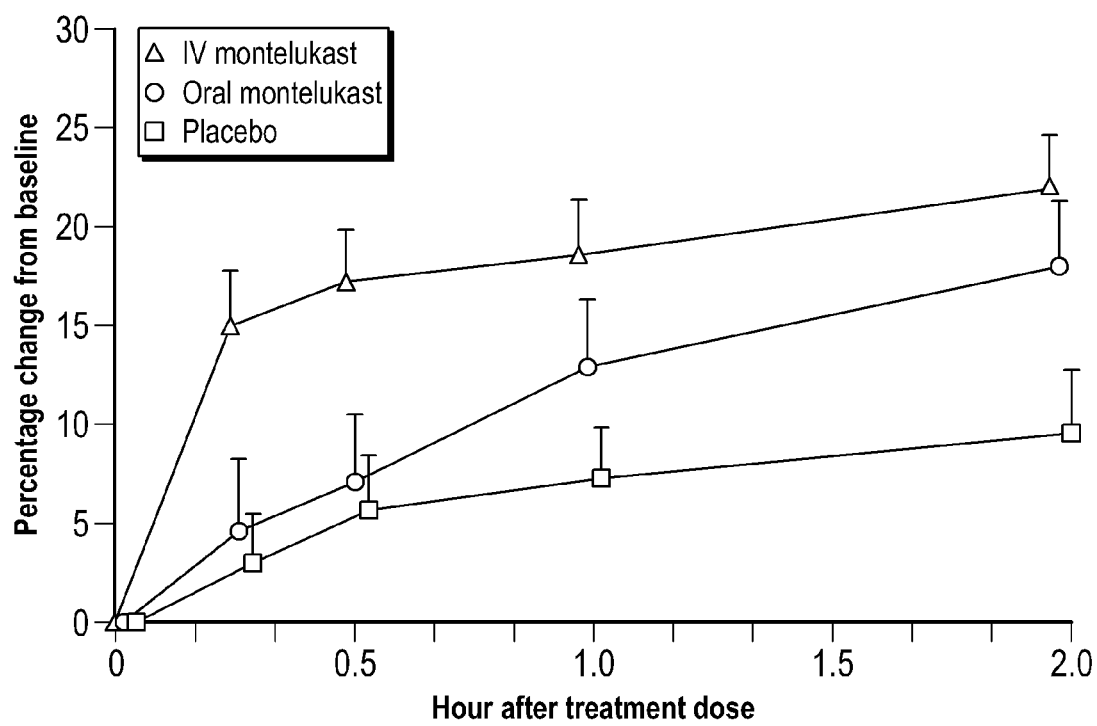
FIG. 7 shows a diagram that compares the effects of intravenous and oral montelukast on airway function.

The use of levocetirizine plus montelukast fills an unmet need in this area of critical care medicine. Without being bound to a particular theory, levocetirizine is not only an effective antihistamine but also acts at physiologic doses to block IL-8 (Interleukin-8). Il-8 is the signaling protein (chemokine) which regulates the influx of neutrophils witnessed in the acute phase of ALI/ARDS. Moreover, levocetirizine blocks IL-6 (Interleukin-6), the signaling protein which acts as a major mediator of both the acute phase response to injury and fever. Montelukast is a safe, effective leukotriene receptor antagonist and blocks the action of LTD4, the most potent of the cysteinyl leukotrienes in contracting smooth airway muscle. Given orally or intravenously, a 15% improvement in the FEV1 (forced expiratory volume at 1 sec) can be realized in minutes to hours as shown in FIG. 7.

Without being bound to a particular theory, both molecules act synergistically to decrease eosinophil quantity and/or migration, where the eosinophil is considered the hallmark of the inflammation. As Pregnancy Category B medications, the combination of levocetirizine plus montelukast can be used safely in a myriad of ICU clinical settings to augment existing treatment protocols, thereby decreasing morbidity/mortality.

As discussed further in Example 2 below, the combination of levocetirizine and montelukast will decrease the requirement for operative procedures such as bronchoscopy and tracheotomy by facilitating early extubation. This in turn will lead to a reduction in complications commonly found in the Intensive Care Unit, e.g., nosocomial infection, pneumothorax secondary to mechanical ventilation, thromboemboli, secondary bleeding, stress and decubitus ulcers. Foreshortened lung and CNS (central nervous system) healing times will effectively decrease the length of the hospital stays and reduce the requirement for digital imaging and revision surgery in addition to the nonexclusive list of complications previously mentioned. Patients will benefit from improved lung function and neurological outcomes. For example, as shown in example 2, the patient with a closed head injury and moderate ARDS by international criteria was treated with a combination of levocetirizine plus montelukast via nasogastric tube. He was extubated on day 2 and discharged from the hospital on day 4. The statistical mean time for intubation alone in this category of lung injury is 7 days.

Advantageously, the use of glucocorticoids can be avoided. Moreover, the combinations of levocetirizine and montelukast can be used safely in conjunction with many existing treatment protocols (e.g., acute brain injury, acute lung injury, acute stroke, meningitis, pneumonia, sepsis). For example, typical antibiotics can be administered to a patient in combination with levocetirizine and montelukast; such antibiotics include but are not limited to vancomycin, meropenem, amoxicillin/beta clauvulanic acid, levofloxacin, piperacillin/tazobactam, ceftriaxone, clindamycin, azithromycin, trimethoprim/sulfamethoxazole, doxycycline or combinations thereof. Additional agents would also include, but are not limited to, the broad spectrum of antibiotics, antivirals, anti-parasitics and antifungals. Moreover, given the excellent safety profiles of both levocetirizine and montelukast, the combination can be administered with many common classes of medications used in an intensive care, hospital or outpatient setting, including but not limited to the vasopressors, diuretics, anticoagulants, anti-seizure medications, proton pump inhibitors, glucocorticoids (if necessary), H2 receptor antagonists, antipyretic agents, anti-inflammatories and anti-neoplastic drugs. There are very few acute/critical care medications that would pose a major treatment problem (e.g. significant drug interaction) other than a dose adjustment to allow for underlying liver or kidney failure.

The combination of levocetirizine and montelukast may be administered to the patient by one or more of the routes, such as enteral, intraperitoneal, inhalation, intramuscular, subcutaneous and oral. Furthermore, the combination of levocetirizine and montelukast may be administered intravenously, for example, to quickly deliver the combination as an emergency combination.

As will be readily apparent to one skilled in the art, the useful in vivo dosage of levocetirizine and montelukast to be administered and the particular mode of administration will vary depending upon the age, weight, medical condition of the patient, the severity of the condition to be treated, the route of administration, the renal and hepatic function of the patient, and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Advantageously, compounds of the present embodiments may be administered, for example, in a single daily dose, or the total daily dosage may be administered in divided doses of two, three or four times daily.

Definitions

The term "effective amount" includes an amount effective, at dosages and for periods of time necessary, to achieve the desired result, e.g., sufficient to treat lung and/or brain injuries. An effective amount of levocetirizine and montelukast may vary according to factors such as the disease state, age, and weight of the subject, and the ability of levocetirizine and montelukast to elicit a desired response in the subject. Dosage regimens may be adjusted to provide the optimum therapeutic response. An effective amount is also one in which any toxic or detrimental effects (e.g., side effects) of levocetirizine and montelukast are outweighed by the therapeutically beneficial effects.

"Ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between any two of these values. Such improvement or change may be observed in treated subjects as compared to subjects not treated with levocetirizine and montelukast, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s), by detection of respiratory or inflammatory disorders in a subject, and/or by modalities such as, but not limited to photographs, video, digital imaging and pulmonary function tests. Amelioration may be transient, prolonged or permanent or it may be variable at relevant times during or after levocetirizine and montelukast are administered to a subject or is used in an assay or other method described herein or a cited reference, e.g., within timeframes described infra, or about 1 hour after the administration or use of levocetirizine and montelukast to about 28 days, or 1, 3, 6, 9 months or more after a subject(s) has received such treatment.

The "modulation" of, e.g., a symptom, level or biological activity of a molecule, or the like, refers, for example, to the symptom or activity, or the like that is detectably increased or decreased. Such increase or decrease may be observed in treated subjects as compared to subjects not treated with levocetirizine and montelukast, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively, e.g., by the subject's self-assessment, by a clinician's assessment or by conducting an appropriate assay or measurement, including, e.g., quality of life assessments, suitable assays for the level or activity of molecules, cells or cell migration within a subject and/or by modalities such as, but not limited to photographs, video, digital imaging and pulmonary function tests. Modulation may be transient, prolonged or permanent or it may be variable at relevant times during or after levocetirizine and montelukast are administered to a subject or is used in an assay or other method described herein or a cited reference, e.g., within times described infra, or about 1 hour after the administration or use of levocetirizine and montelukast to about 3, 6, 9 months or more after a subject(s) has received levocetirizine and montelukast.

As used herein, the terms "prevent," "preventing," and "prevention" refer to the prevention of the recurrence, onset, or development of lung and/or brain injury. Preventing includes protecting against the occurrence and severity of upper and/or lower respiratory tract infections.

As used herein, the term "prophylactically effective amount" refers to the amount of a therapy (e.g., a pharmaceutical composition comprising montelukast and levocetirizine) which is sufficient to result in the prevention of the development, recurrence, or onset of lung and/or brain injury or to enhance or improve the prophylactic effect(s) of another therapy.

As used herein, "subject" includes organisms which are capable of suffering from lung and/or brain injury or other disorder treatable by a combination of montelukast and levocetirizine or who could otherwise benefit from the administration of montelukast and levocetirizine as described herein, such as human and non-human animals. Preferred human animals include human subjects. The term "non-human animals" includes all vertebrates, e.g., mammals, e.g., rodents, e.g., mice, and non-mammals, such as non-human primates, e.g., sheep, dog, cow, chickens, amphibians, reptiles, etc.

The following Examples are presented for the purposes of illustration and should not be construed as limitations.

EXAMPLES

Example 1

Case Study: 18-year-old male trauma patient with brain, lung, facial and liver injuries

| Patient | CR |
|---|---|
| DOB | Jun. 14, 1993 |
| Age | 18 |

The patient is a 18-year-old male seen and evaluated in the Santa Barbara Cottage Hospital Surgical ICU after falling off a cliff in Isla Vista, Calif. at approximately midnight Feb. 17, 2012. The estimated height of the fall was 30-35 feet. His Glasgow Coma scale on admission was 7/15, reflecting a greater than fifty percent chance of mortality. Contributing factor: alcohol with the consumption of 10 drinks between 9 PM and midnight. (BAC 0.252 g/dL).

Social History: student at the University of California, Santa Barbara

Pre-existing Major Medical Problems: none

Pertinent Physical Examination:

At the time of the consultation, Saturday Feb. 18, 2012 (10:30-13:15 hours) CR was intubated and sedated on a ventilator.

Vital signs: Temperature 36.9° C. B/P 95/39 mm Hg Pulse 76 beats/min

Respiratory rate controlled 20/minute

Tidal volume 500 ml FiO2 (inspired oxygen) 40%. PEEP: 5 cm H2O

Weight: 73 kg Height: 177.8 cm

HEENT:

| Ears: | gray tympanic membranes, no hemotympanum noted |
|---|---|
| Nose: | serosanguinous drainage right. Laceration of the right nasolabial groove - sutured |
| Throat: | intubated |
| Eyes: | right upper lid ecchymosis |
| Face: | equivocal depression of the right cheek |
| Lungs: | decreased breath sounds in the right lower lung field |
| Heart: | S1, S2 distinct, no pathological murmur |

Laboratory Data:

Feb. 18, 2012 at 11:13 hours

Arterial blood gases: pH 7.28, PaO2 129 mm Hg, FiO2 0.40, PaCO2 41 mm Hg

WBC: 19,100 cells/µL, hemoglobin 11.8 g/dL, hematocrit 33.3%, platelet count 253,000/µL BAC (blood alcohol content) 0.252 g/dL at 12:40 hours PT 12.8 sec., PTT 30.1 sec. at 04:55 hours sodium 139 mEq/L, potassium 4.0 mEq/L, chloride 109 mEq/L, bicarbonate 19 mEq/L, BUN 17 mg/dL, creatinine 0.83 mg/dL Imaging: Reviewed with Radiology: Hospital Day #1

CT Scan of the head without contrast 01:10, Feb. 18, 2012: Contusions of the frontal lobes with punctate hemorrhages, right greater than left.

CT Scan of the face 01:10, Feb. 18, 2012: multiple comminuted fractures

Nasal bones

Right maxillary sinus with fat herniating from the right orbit into the ethmoid sinus, as well as inferiorly into the maxillary sinus, i.e., blowout fracture ~1.25 cm Fracture of the lateral and medial walls of the right maxillary sinus; nondisplaced fracture of the right zygoma.

CT Scan of the chest, abdomen and pelvis: 01:18 hours, Feb. 18, 2012: compatible with aspiration pneumonia, right greater than left, i.e., dense consolidations within the dependent portions of the lungs right greater than left and ground glass opacities within the anterior aspects of the lungs bilaterally as well as debris seen within the distal bronchioles consistent with aspiration Abdomen and pelvis: questionable focal laceration of the lateral lobe of the liver Neck: no fractures delineated. Straightening of the usual cervical lordosis Assessment: 18 year old male status post ~30-35 foot fall from a cliff in Isla Vista, Ca. just before midnight, Feb. 17, 2012.

Multiple facial fractures as delineated
    Frontal lobe contusions of the brain, right greater than left
    Aspiration pneumonia, right greater than left
    Focal laceration of the right lobe of the liver Treatment Regimen:

| | |
|---|---|
| Trauma Protocol for severe brain injury: | Induced coma with external ventricular drain |
| | Licox (brain tissue oxygen) monitoring |
| | Intravascular central cooling catheter |
| Prophylactic antibiotic coverage to include: | vancomycin and meropenem to cover opportunistic pathogens associated with the brain, lung and facial injuries |
| Levocetirizine 5 mg per nasogastric tube/orally every 12 hours × 2, then every 24 hours plus montelukast 10 mg per nasogastric tube/orally every 12 hours × 2, then every 24 hours initiated Feb. 19, 2012 (hospital day #2) through Mar. 4, 2012 (hospital #16: 15 days of therapy) | abort the inflammatory response in the brain and face address the acute lung injury without the use of steroids. |

Steroids in this critical care setting have been correlated with an increased risk of secondary infection with an associated increase in morbidity and mortality.

Clinical Course (Lung):

The patient underwent two bedside bronchoscopies, the first of which only identified thick secretions in the lower airway the evening of Feb. 19, 2012, hospital day #2. Increasing deterioration with an associated PaO2/FiO2 of 247.4 (Berlin definition of mild ARDS) led to the administration of levocetirizine and montelukast therapy via nasogastric tube the evening of Feb. 19, 2012, hospital day #2.

Figure 2A:
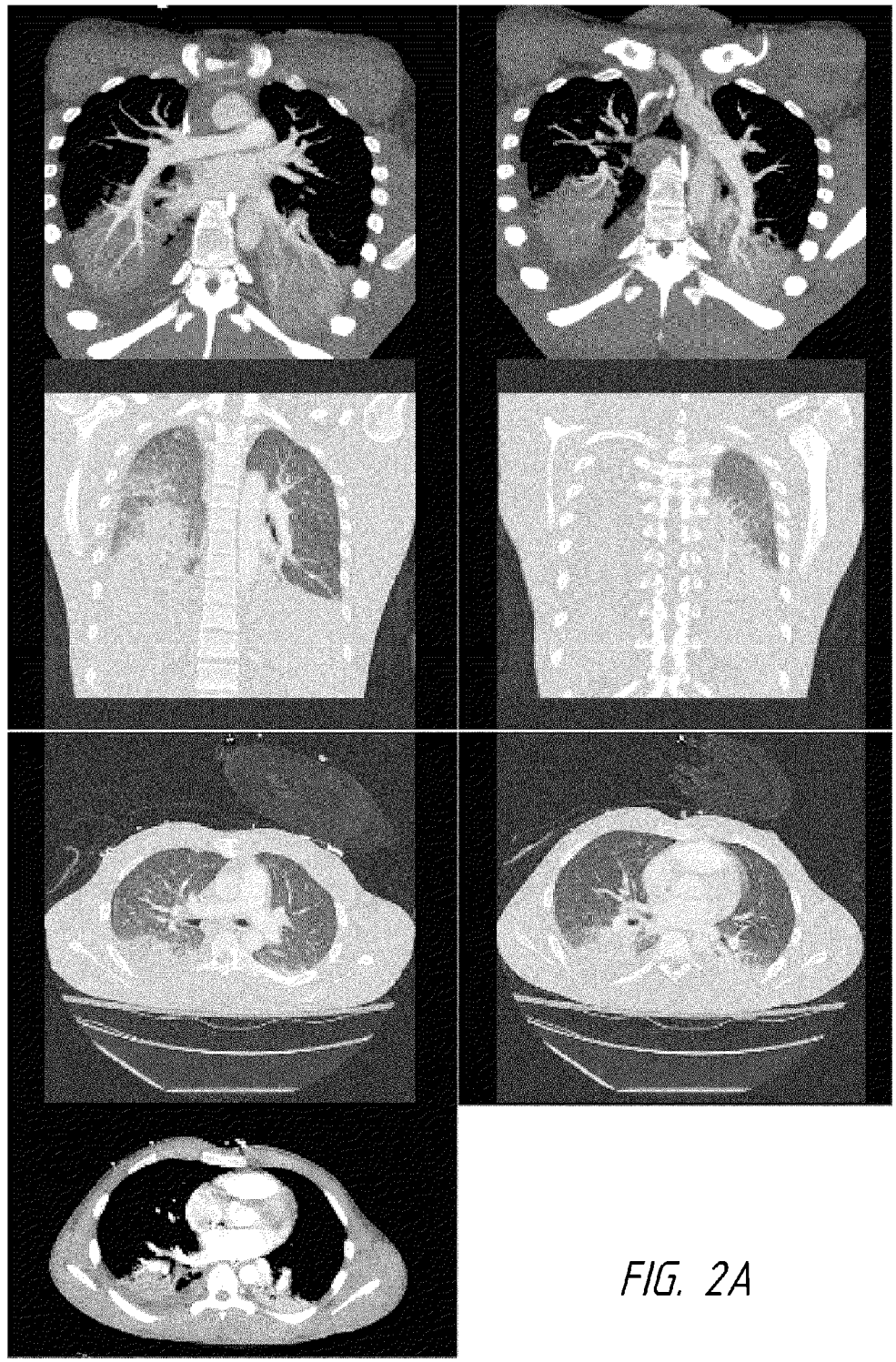
FIGS. 2A-B show digital radiographic CT images of a patient.

A CT scan of the patient's chest (depicted in FIG. 2A) taken at 09:30 hours, Feb. 21, 2012, hospital day #4, 36 hours into therapy, revealed: (1) a patchy infiltrate in the right upper lobe with a multinodular appearance and denser consolidation in the right lower lobe, suggesting multifocal pneumonia. Aspiration could not be ruled out. (2) Noted as well were small bilateral pleural effusions, right greater than left with (3) consolidation in the posterior left lower lobe indicating atelectasis or a third area of pneumonia. There was no CT evidence of pulmonary embolism. Armed with this data, a second bronchoscopy was performed on Feb. 21, 2012, hospital day #4, which identified and extracted significant food foreign bodies, particularly in the right mainstem bronchus. Thereafter, the patient rapidly improved as predicted under the umbrella of levocetirizine plus montelukast and was extubated at 09:30 hours, Feb. 23, 2012, hospital day #6.

Figure 3:
FIG. 3 shows a chest x-ray image taken of the patient, hospital day #8 and 5.5 days on combined therapy. The bibasilar opacities have almost completely resolved (See Example 1).

A follow-up chest x-ray on Feb. 25, 2012, hospital day #8 (depicted in FIG. 3) demonstrated nearly resolved bibasilar opacities (and thus likely reflecting volume loss) with no blunting of the costophrenic angles (otherwise reflecting fluid or atelectasis). The x-ray also showed no new infiltrate, effusion, or congestive heart failure. The left subclavian line remained in place.

The rapid resolution of the aspiration pneumonia was aided by the use of levocetirizine plus montelukast (significantly shorter clearing time by several days when compared to conventional therapy, i.e., almost complete clearing between day #4, the day of the foreign body removal and day #8) using imaging as an objective marker. No additional pulmonary intervention was required during the hospitalization.

Figure 2B:
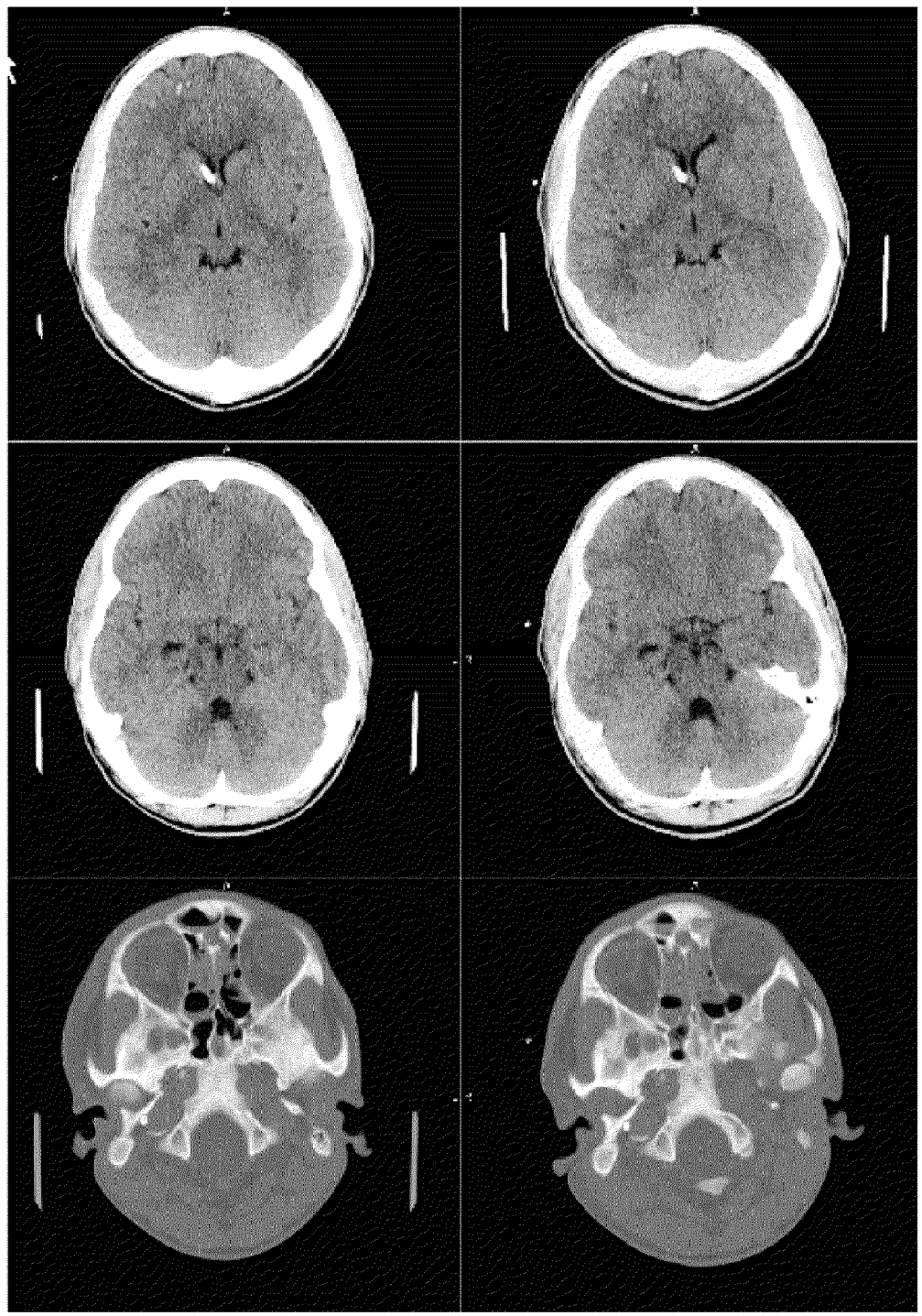

Clinical Course (Brain):

The patient was weaned from sedation on Feb. 22, 2012, post injury day #4. A CT scan of the patient's brain, taken 0243 hours, Feb. 22, 2012, (as shown in FIG. 2B) demonstrated the following: (1) slight interval improvement of the multiple nodular densities throughout the frontal lobes, bilaterally consistent with parenchymal contusions; stable cerebral edema within the inferior frontal lobes bilaterally; (2) stable right frontal approach ventriculostomy catheter tip in the right lateral ventricle and pressure monitor within the right frontal lobe; (3) multiple facial fractures as better seen on prior CT Scan of the face; and (3) stable paranasal sinuses.

The findings reflect an enhanced clinical response (foreshortened healing time) in less than 2.5 days following the addition of levocetirizine+montelukast (Feb. 19, 2012 PM, hospital day #2) to the brain trauma protocol. An even more robust response would be realized from the combination of IV levocetirizine+montelukast (currently not available) given on presentation to the Emergency Room (time zero).

The patient was extubated at 09:30 hours, Feb. 23, 2012 post injury day #5 despite the aspiration and two bronchoscopies. He emerged from the coma, was stabilized and was transferred Mar. 2, 2012, hospital day #14 to the Cottage Rehabilitation Hospital at essentially a Rancho 4 level of cognitive function. Maxillofacial fractures were corrected on Mar. 1, 2012 prior to transfer. He was discharged Mar. 14, 2012 to his parents for travel home to the East Coast.

On admission to Cottage Rehabilitation Hospital, CR's functional status showed him to be supervised for feeding. Grooming was minimally assisted. Bathing was minimally assisted. Upper and lower body dressing were supervised. He was able to manage his own bowel and bladder, but did require supervision due to some impulsivity. He was supervised for transfers. He was rather impulsive and had a strong drive to continue ambulating. It was very difficult for him to sit down and relax. He did complain of diplopia on admission, but this improved throughout the course of the hospitalization. His memory was moderately impaired as was decision-making and problem-solving. Initially he had very poor memory and poor carryover from session to session and day-to-day.

By discharge, he required minimal prompting for memory and minimal direction for problem-solving. Social interactions were modified independent.

A telephone discussion with both parents on May 8, 2012 confirmed their son was doing well and would return to both school and sports in the fall of 2012.

Overview:

This case is a clinical example of the remarkable anti-inflammatory synergy between two extremely safe molecules: levocetirizine plus montelukast for the treatment of acute lung and brain injury. There were no complications from twice daily and daily dosing administered during the initial fifteen day period of his hospital/rehabilitation stay.

Example 2

Case Study: 19 year old male with aspiration pneumonia/pulmonary contusion/closed head injury

| | |
|---|---|
| Patient | EL |
| DOB | Aug. 14, 1993 |
| Age | 19 |

The patient is a 19 year old male status post 20 foot fall from a building in Isla Vista, Calif. at 01:00 hours, Sunday, Oct. 28, 2012, with resultant significant mid-facial fractures, lung contusion, aspiration and closed head injury. The Glasgow Coma Scale as an index of consciousness at the scene was 3/15 (normal 15/15). He had no spontaneous movement and appeared to have severe facial trauma. EL was subsequently transported via ambulance to the Santa Barbara Cottage Hospital Emergency Room for evaluation and admission. At the time of the initial Otolaryngology evaluation he was intubated on a respirator in the SICU (Surgical Intensive Care Unit). Respirator settings were as follows: FIO2 60% (inspired oxygen), PEEP five cm H2O, tidal volume 500 ml, SMIV, pressure support 10 cm H2O Vital signs: Temperature 100.5° F./38.1° C. Heart rate 114 beat/min Respiratory rate 29-32 breaths/minute B/P 117/50 mmHg Weight 58 kg Height 167 cm BMI 24.2

HEENT:

| | |
|---|---|
| Ears | AS (left): gray tympanic membrane, AD (right): scant hemotympanum |
| Nose | occlusion of the left anterior airway from swelling of the left inferior turbinate and deviated nasal septum. |
| Throat | endotracheal tube and orogastric tube in place |
| Neck | without adenopathy |
| Lungs | Bilateral rhonchi |
| Heart | tachycardia/regular rhythm |
| Abdomen | flat |
| Neuro | Intubated/sedated |

Preadmission medications: none
Past surgical history: none
Major medical problems: none
Social History: student at Cal Lutheran
Allergies to Medication: none Laboratory Data: at 0456 hours, Oct. 28, 2012: white count 5000 cells/μL, hemoglobin 15.1 g/dL, hematocrit 45.3%, platelet count 171,000/μL. troponin less than 0.03 μg/L. sodium 137 mEq/L, potassium 3.3 mEq/L, chloride 106 mEq/L, bicarbonate 22 mEq/L, BUN 11 mg/dL, creatinine 0.7 mg/dL, glucose 138 mg/dL. BAC (blood alcohol content) 0.225 g/dL Arterial blood gases at noon, Sunday, Oct. 28, 2012: FIO2 0.50, pH 7.28, PaCO2 30 mm Hg, PaO2 68 mm Hg, bicarbonate 14 mEq/L. (Berlin definition of moderate ARDS—anticipated mean intubation period of 7 days)

Figure 4:
FIG. 4 shows digital radiographic CT images taken of the chest of a nineteen year old male with aspiration pneumonia and pulmonary contusion shortly after presentation to the hospital (See Example 2). The CT image is consistent with pulmonary contusion and aspiration prior to treatment.
Figure 5A:
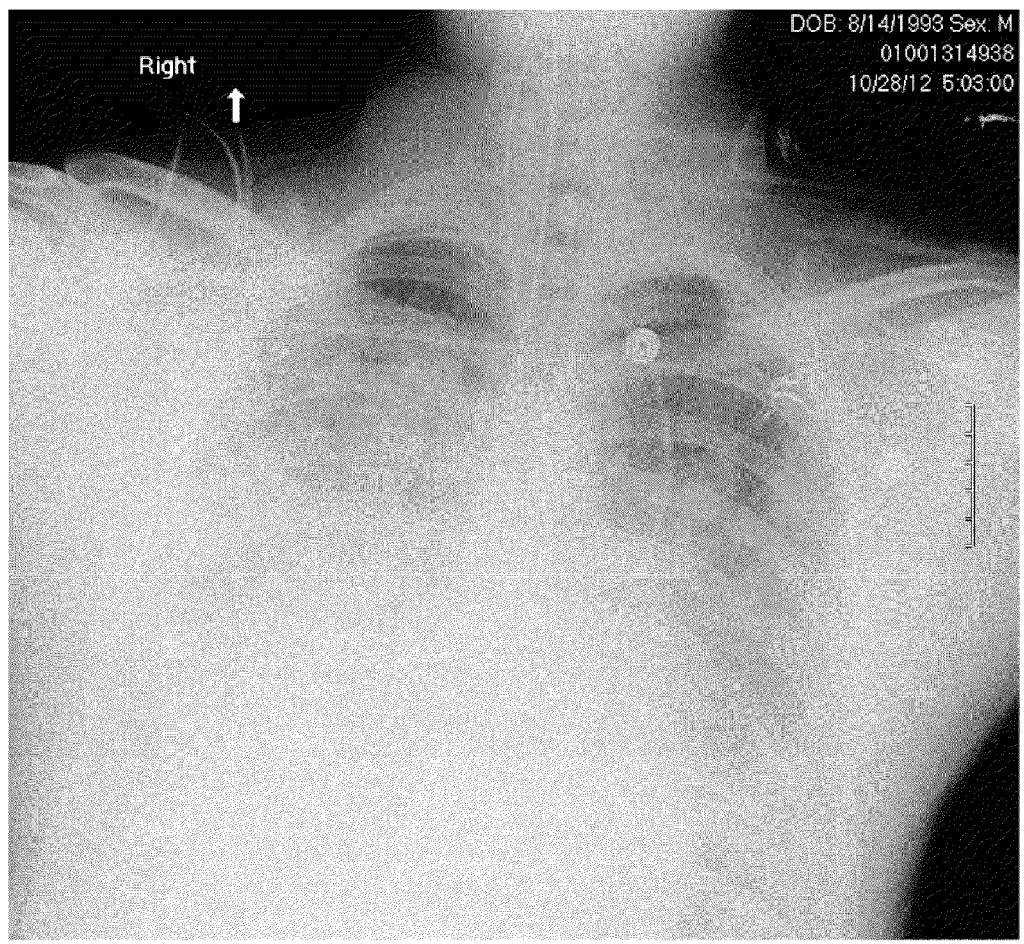
FIGS. 5A-B show x-ray images of the chest of a nineteen year old male patient. The patient had aspiration pneumonia and pulmonary contusion (See Example 2).

Imaging: reviewed with radiology the morning of Oct. 28, 2012:

CT Scan of the Brain and Facial Bones 0152 hours, Oct. 28, 2012:

No acute intracranial pathology identified.
Soft tissue swelling of the right cheek.
Old septal fracture—right.
New comminuted nasoseptal fracture.
Fracture of the right lamina papyracea.
Fracture of the lateral wall of the left maxilla.
Air in the right orbit.
Blood in the nasal airway, ethmoid sinuses, left frontal sinus and left maxillary sinus.
C-spine 01:52 hours, Oct. 28, 2012: no fracture.
Chest x-ray 02:50 hours, Oct. 28, 2012: bilateral infiltrates. A second chest x-ray taken at 0503 hours, Oct. 28, 2012, prior to the initiation of therapy, is depicted in FIG. 5A.
CT Scan of the chest: 01:59 hours., Oct. 28, 2012: demonstrated bilateral pulmonary contusions/aspiration (as shown in FIG. 4).
X-ray of the pelvis 01:33 hours, Oct. 28, 2012: negative for fracture.
Antibiotics: Vancomycin 1 gram IV q 8 hours, Zosyn® (piperacillin/tazobactam) 3.375 mg IV q 6 hours representing standard therapy for listed injuries (open facial trauma+ aspiration pneumonia)

Plan:
Baseline CRP (C-reactive protein) and SED (sedimentation) Rate
Levocetirizine 5 mg per orogastric tube q 12 hours×2 doses, followed by 5 mg q 24 hours×10 days.
Montelukast 10 mg per orogastric tube q 12 hours×2 doses, followed by 10 mg q 24 hours The combination of levocetirizine and montelukast was administered to achieve steady state levels at ~24 hours (as opposed to ~40 hours); synergistically block the acute inflammatory response without using steroids.

Figure 5B:
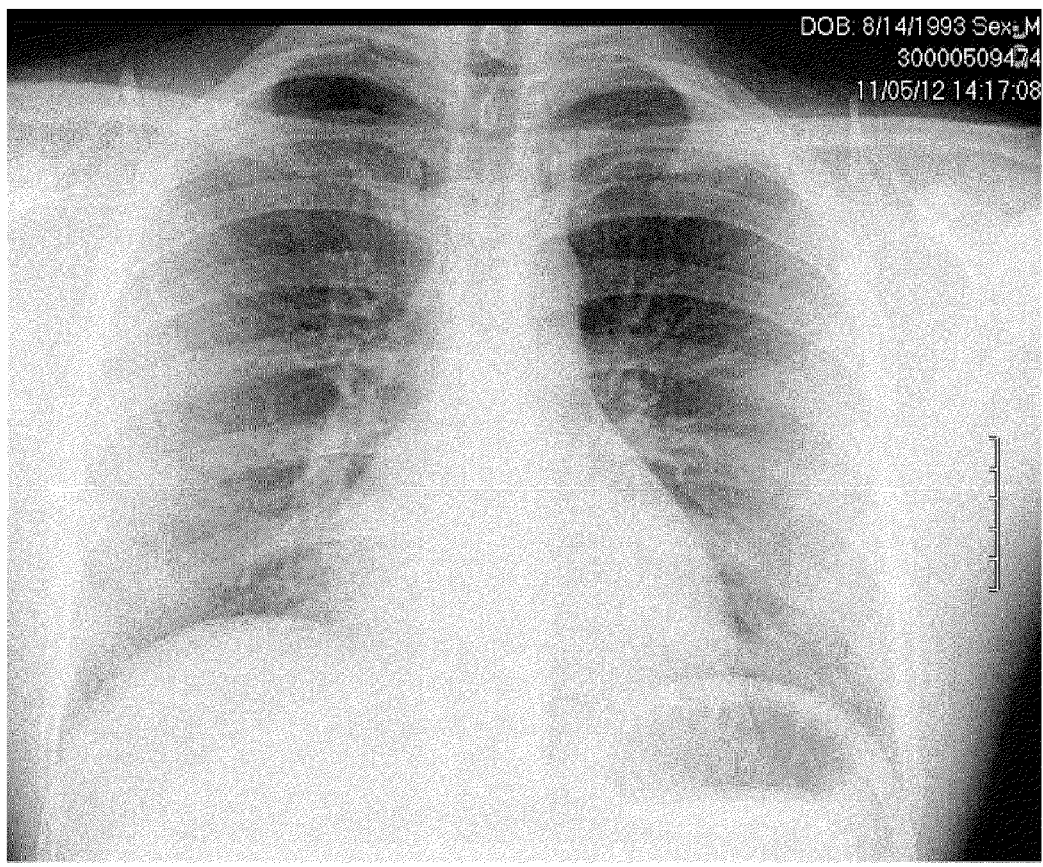

Hospital Course:

The patient made a remarkable recovery on the aforementioned protocol. He was extubated on hospital #2, Oct. 29, 2012, transferred to the floor on hospital day #3, Oct. 30, 2012, and discharged home on day #4, Oct. 31, 2012. Augmentin® (amoxicillin/beta-clavulanic acid) and Levaquin® (levofloxacin) antibiotics were continued on an outpatient basis, as well as the levocetirizine and montelukast. His nasoseptal fracture was set in outpatient surgery Nov. 7, 2012. A chest x-ray on Nov. 5, 2012, post injury day #8, (FIG. 5B) objectively shows the patient's lungs have cleared, demonstrating the resolution of the lung contusion/bilateral pulmonary infiltrates.

Overview:

This case is an example of the remarkable anti-inflammatory synergy between two extremely safe molecules: levocetirizine plus montelukast in the treatment of acute lung injury. No interval bronchoscopy was needed, and there were no complications from the major trauma. In addition to a foreshortened lung recovery time (8 days) as opposed to two to three weeks, the lungs cleared without bronchoscopic intervention for culture/debridement and there were no complications in this critically ill patient.

The patient was extubated hospital day #2 and discharged hospital day #4. The mean intubation time alone for moderate ARDS as delineated by the Berlin definition is 7 days with an associated risk of mortality of 32%.

Example 3

Prophetic Study: Patients with mild, moderate, and severe Adult Respiratory Distress Syndrome.

In this study, the combination of levocetirizine and montelukast is administered to patients suffering from mild Adult Respiratory Distress Syndrome (ARDS), patients suffering from moderate ARDS, and patients suffering from severe ARDS. The following particular parameters are monitored:

length of hospital stay, number of days on a ventilator (intubated), mortality, and secondary infection. All patients are given the combination of levocetirizine and montelukast upon presentation. Given the intrinsic safety of the molecules and synergistic manner in which multiple pathways are blocked during the acute or innate phase response to trauma, an initial group of 20 patients are compared with retrospective data gleaned from patients treated with existing protocols.

Anticipated Outcomes Include the Following

Reduced intubation time when compared to patients exhibiting the same or similar degrees of injury and the same Berlin classification;

Reduced length of hospital stay;

Decreased mortality; and

Decreased number of nosocomial infections.

The Combination of Levocetirizine and Montelukast

Without being bound to a particular theory, it is believed that montelukast alone would improve lung function and potentially decrease total intubation times while levocetirizine would not be potent enough by itself to clear a patient's lungs. However, the combination of levocetirizine and montelukast exhibits synergy to effectively treat ARDS and its related symptoms in the three classes of patients identified above (mild, moderate, severe).

The effect can be reasonably extrapolated from the cell science. Levocetirzine blocks the acute or innate phase response to injury not only as an antihistamine but through its anti-inflammatory properties which include in part, the modulation of toll-like receptors, Interleukin 6 (IL-6) and Interleukin 8 (IL-8). IL-6 is one of the most important mediators of the acute phase reaction to injury and fever.

Moreover, autopsy specimens gleaned from the lungs of patients who have died from ARDS, both primarily and secondarily from their trauma, are underscored by the presence of neutrophils. Levocetirzine blocks IL-8, the signaling protein responsible for chemotaxis in target cells, primarily neutrophils, causing them to migrate to the site of injury. In addition to neutrophils there are a wide range of other cells, e.g., endothelial cells, mast cells, macrophages, and keritinocytes that respond to IL-8 as well. Montelukast block the actions of LTD4 at the receptor. Leukotriene D4 is most potent of the cysteinyl leukotrienes in contracting airway smooth muscle. It promotes the recruitment of eosinophils, dendritic cells (antigen presenting cells) and T cells, which in turn in increases cell recruitment and activation. Clinically, montelukast has been shown to increase FEV 1 (forced expiratory volume in the first second of expiration) by 15% in minutes to hours following administration.

Both levocetirizine and montelukast affect eosinophil quantity/migration. An eosinophilic infiltrate is considered a hallmark of inflammation.

Thus, given the multiple sites of action within the inflammatory pathway underscored by the safety of the molecules, the combination of levocetirizine and montelukast will improve outcomes over existing protocols, and decrease morbidly and mortality in this patient population.

Example 4

Prophetic Study: Patients with acute brain injury/traumatic brain injury

In this study, the combination of levocetirizine and montelukast is administered to patients suffering from acute brain injury or patients suffering from traumatic brain injury.

The following particular parameters are monitored: LICOX (brain tissue O2 and temperature data), a neurological baseline assessment and corresponding data taken after patients have been treated with the combination of levocetirizine and montelukast for 30 days, the Glasgow Coma Scale (statistically significant for mortality in the first two weeks of hospitalization), APACHE III scores (statistically significant for mortality after two weeks of hospitalization), length of hospital stay, number of days on a ventilator (intubated), mortality, and secondary infection. All patients are given the combination of levocetirizine and montelukast upon presentation. Given the intrinsic safety of the molecules and synergistic manner in which multiple pathways are blocked during the acute or innate phase response to trauma, an initial group of 20 patients are compared with retrospective data gleaned from patients treated with existing protocols.

Anticipated Outcomes Include the Following:

Improved neurological function using standard measures of cognitive function

Reduced intubation time when compared to patients exhibiting the same or similar degrees of injury and the same Berlin classification.

Reduced length of hospital stay

Decreased mortality

Decreased number of nosocomial infections

The Combination of Levocetirizine and Montelukast

Without being bound to a particular theory, it is believed that montelukast alone would have minimal effect while levocetirizine would decrease swelling and limit tissue hypoxia/ischemia. By comparison, the combination of levocetirizine and montelukast safely exhibits a remarkable synergy to effectively treat acute brain injury or traumatic brain injury and their related symptoms.

The effect can be reasonably extrapolated from the cell science. Levocetirzine blocks the acute or innate phase response to injury not only as an antihistamines but through its anti-inflammatory properties which include in part, the modulation of toll-like receptors, IL-6 and IL-8. IL-6 is one of the most important mediators of the acute phase reaction to injury and fever. Importantly, IL-6 is capable of crossing the blood-brain brain, which makes it a significant cytokine even in the presence of a less severe, closed head injury.

Autopsy specimens gleaned from the lungs of patients who have died from ARDS, both primarily and secondarily from their trauma, are underscored by the presence of neutrophils. Levocetirzine additionally blocks IL-8 (Interleukin 8), the signaling protein responsible for chemotaxis in target cells, primarily neutrophils, causing them to migrate to the site of injury. In addition to neutrophils there are a wide range of other cells, e.g., endothelial cells, mast cells, macrophages, and keritinocytes that respond to IL-8 as well.

Montelukast block the actions of Leukotriene D4 (LTD4) at the receptor. LTD4 is the most potent of the cysteinyl leukotrienes in contracting airway smooth muscle. It promotes the recruitment of eosinophils, dendritic cells (antigen presenting cells) and T cells, which in turn in increases cell recruitment and activation. Clinically, montelukast has been shown to increase FEV1 by 15% in minutes to hours following administration.

Both levocetirizine and montelukast affect eosinophil quantity/migration. An eosinophilic infiltrate is considered a hallmark of inflammation.

In conclusion, given the multiple sites of action within the inflammatory pathway underscored by the safety of the molecules, the combination of levocetirizine and montelukast will improve outcomes over existing protocols, and decrease morbidity and mortality in this patient population.

What is claimed is:

1. A method of treating traumatic lung injury or a symptom of traumatic lung injury in a patient in need thereof comprising administering an effective amount of a combination of levocetirizine and montelukast wherein the traumatic lung injury is a lung contusion.

2. The method of claim 1, wherein the traumatic lung injury is the result of a primary injury during a traumatic event resulting in physical damage.

3. The method of claim 1, wherein the combination is administered at the onset of symptoms.

4. The method of claim 1, wherein the combination is administered at the time of diagnosis.

5. The method of claim 1, wherein the combination is administered in a sequential manner.

6. The method of claim 1, wherein the combination is administered in a substantially simultaneous manner.

7. The method of claim 1, further comprising the administration of an additional active agent.

8. The method of claim 7, wherein the additional active agent is selected from the group consisting of an antibiotic, antiviral, anti-parasitic, antifungal, vasopressor, diuretic, anticoagulant, anti-seizure medication, proton pump inhibitor, H2 receptor antagonist, antipyretic agent, anti-inflammatory drug, anti-neoplastic drug, and combinations thereof.

9. The method of claim 8, wherein the additional active agent is an antibiotic selected from the group consisting of vancomycin, meropenem, amoxicillin/beta clauvulanic acid, levofloxacin, piperacillin/tazobactam, ceftriaxone, clindamycin, azithromycin, trimethoprim/sulfamethoxazole, doxycycline or combinations thereof.

10. The method of claim 1, wherein the combination is administered to the patient by one or more of the routes consisting of enteral, intravenous, intraperitoneal, inhalation, intramuscular, subcutaneous and oral.

11. The method of claim 1, wherein the levocetirizine and montelukast are administered by the same route.

* * * * *